United States Patent
Lerner et al.

(10) Patent No.: US 11,419,969 B2
(45) Date of Patent: Aug. 23, 2022

(54) NEONATAL AND PEDIATRIC BLOOD FILTRATION SYSTEM

(71) Applicant: Nuwellis, Inc., Eden Prairie, MN (US)

(72) Inventors: David Lerner, St. Paul, MN (US); David Haskvitz, Maple Grove, MN (US); Franz Willems Ulrich, Minneapolis, MN (US)

(73) Assignee: Nuwellis, Inc., Eden Prairie, MN (US)

( * ) Notice: Subject to any disclaimer, the term of this patent is extended or adjusted under 35 U.S.C. 154(b) by 0 days.

(21) Appl. No.: 17/309,536

(22) PCT Filed: Mar. 26, 2020

(86) PCT No.: PCT/US2020/024974
§ 371 (c)(1),
(2) Date: Jun. 3, 2021

(87) PCT Pub. No.: WO2020/198483
PCT Pub. Date: Oct. 1, 2020

(65) Prior Publication Data
US 2022/0001088 A1    Jan. 6, 2022

Related U.S. Application Data

(60) Provisional application No. 62/823,913, filed on Mar. 26, 2019.

(51) Int. Cl.
*A61M 1/34*    (2006.01)

(52) U.S. Cl.
CPC ........ *A61M 1/3482* (2014.02); *A61M 1/3441* (2013.01); *A61M 2202/0415* (2013.01);
(Continued)

(58) Field of Classification Search
CPC .. A61M 2205/3334; A61M 2205/3337; A61M 2205/3355; A61M 2240/00;
(Continued)

(56) References Cited

U.S. PATENT DOCUMENTS 5,932,103 A * 8/1999 Kenley ............... A61M 1/3441
                                                        210/646
6,471,872 B2   10/2002 Kitaevich et al.
(Continued)

FOREIGN PATENT DOCUMENTS

CN    102895711 A    1/2013
CN    106215263 A    12/2016
(Continued)

OTHER PUBLICATIONS

"International Application Serial No. PCT/US2020/024974, International Preliminary Report on Patentability dated May 6, 2021", 7 pgs.
(Continued)

*Primary Examiner* — Adam Marcetich
(74) *Attorney, Agent, or Firm* — Schwegman Lundberg & Woessner, P.A.

(57) ABSTRACT

A blood filtration system may to couple to an infusion pump that is external to the blood filtration system. The blood filtration system may include a blood circuit, for instance a variable-volume blood circuit. An infusion port may be in communication with the blood circuit and may receive an infusion fluid pumped by the infusion pump. A filtration pump may extract a filtrate fluid from a filter. The filtrate fluid may include filtered plasma constituents. A fluid characteristic sensor may measure one or more of pressure or flow rate of the infusion fluid pumped by the infusion pump. A controller may monitor the fluid characteristic sensor to determine a change in the pressure or flow rate of the infusion fluid. The controller may modulate a speed of the variable-speed filtration pump based on the change in the pressure or flow rate of the infusion fluid.

18 Claims, 15 Drawing Sheets

(52) U.S. Cl.
CPC ............... *A61M 2205/3334* (2013.01); *A61M 2205/3337* (2013.01); *A61M 2205/3355* (2013.01); *A61M 2240/00* (2013.01)

(58) Field of Classification Search
CPC .. A61M 1/342; A61M 1/3424; A61M 1/3431; A61M 1/3434; A61M 1/3437; A61M 1/3441; A61M 1/3444; A61M 1/3448; A61M 1/3451; A61M 2205/17
See application file for complete search history.

(56) References Cited

U.S. PATENT DOCUMENTS

| | | |
|---|---|---|
| 6,561,997 B1 | 5/2003 | Weitzel et al. |
| 8,506,513 B2 | 8/2013 | Rossi et al. |
| 8,888,730 B2 | 11/2014 | Rossi et al. |
| 9,138,526 B2 | 9/2015 | Ware et al. |
| 9,533,087 B2 | 1/2017 | Suffritti et al. |
| 9,872,949 B2 | 1/2018 | Meyer et al. |
| 2001/0037968 A1* | 11/2001 | Bene .................. A61M 1/1607 210/321.71 |
| 2002/0121471 A1 | 9/2002 | Pedrazzi |
| 2004/0011740 A1 | 1/2004 | Bernard et al. |
| 2004/0030277 A1 | 2/2004 | Omahony et al. |
| 2004/0068219 A1* | 4/2004 | Summerton ........ A61M 1/3437 210/321.71 |
| 2004/0129638 A1* | 7/2004 | Chang .................... A61K 45/06 210/646 |
| 2005/0061740 A1 | 3/2005 | Felding et al. |
| 2005/0085760 A1* | 4/2005 | Ware .................... A61M 1/3441 604/4.01 |
| 2006/0009727 A1 | 1/2006 | Omahony et al. |
| 2009/0043240 A1 | 2/2009 | Robinson et al. |
| 2009/0124963 A1* | 5/2009 | Hogard ................ A61M 1/341 604/30 |
| 2009/0152200 A1* | 6/2009 | Lannoy ............... A61M 1/3434 210/201 |
| 2010/0036486 A1* | 2/2010 | Mazur ................. A61M 1/3667 623/3.13 |
| 2012/0073673 A1* | 3/2012 | Kameyama ....... A61M 5/16813 137/14 |
| 2012/0078218 A1* | 3/2012 | Barnes ................ A61M 5/1413 604/500 |
| 2012/0130153 A1* | 5/2012 | Bolyard .................... H02P 6/14 600/17 |
| 2013/0222108 A1 | 8/2013 | Newlin et al. |
| 2013/0299399 A1* | 11/2013 | Suffritti .................. B01D 61/22 210/137 |
| 2015/0034536 A1 | 2/2015 | Rada et al. |
| 2016/0038665 A1 | 2/2016 | Schaefer et al. |
| 2016/0101278 A1* | 4/2016 | Norris ................... A61M 1/288 604/29 |
| 2017/0319768 A1 | 11/2017 | Szpara et al. |
| 2018/0338914 A1* | 11/2018 | Inhaber ................ A61K 31/716 |
| 2019/0231957 A1 | 8/2019 | Burbank et al. |
| 2019/0321621 A1* | 10/2019 | Turner ................ A61M 39/281 |
| 2020/0155745 A1* | 5/2020 | Nilsson ................. A61M 1/304 |
| 2020/0164118 A1* | 5/2020 | Woloszko ........... A61M 3/0241 |
| 2020/0276374 A1* | 9/2020 | Hulme ................. B01D 61/025 |
| 2021/0379262 A1 | 12/2021 | Lerner et al. |

FOREIGN PATENT DOCUMENTS

| | | |
|---|---|---|
| EP | 0373455 A1 | 6/1990 |
| EP | 0830154 A1 | 3/1998 |
| EP | 1104682 A1 | 6/2001 |
| EP | 1235612 B1 | 1/2010 |
| EP | 1356836 B1 | 11/2013 |
| EP | 2227268 B1 | 5/2015 |
| EP | 1998826 B1 | 2/2016 |
| EP | 2714123 B1 | 8/2017 |
| EP | 2950842 B1 | 5/2019 |
| EP | 3484536 A1 | 5/2019 |
| EP | 3142719 B1 | 11/2019 |
| JP | 2011147803 A | 8/2011 |
| WO | WO-9116938 A1 | 11/1991 |
| WO | WO-2015007596 A1 | 1/2015 |
| WO | WO-2015188154 A9 | 4/2016 |
| WO | WO-2018017623 A1 | 1/2018 |
| WO | WO-2020198483 A1 | 10/2020 |

OTHER PUBLICATIONS

"International Application Serial No. PCT/US2020/024974, International Search Report dated Aug. 6, 2020", 4 pgs.

"International Application Serial No. PCT/US2020/024974, Invitation to Pay Additional Fees dated Jun. 9, 2020", 3 pgs.

"International Application Serial No. PCT/US2020/024974, Written Opinion dated Aug. 6, 2020", 10 pgs.

"European Application Serial No. 20776684.1, Extended European Search Report dated Dec. 6, 2021", 8 pages.

"European Application Serial No. 20776684.1, Response filed Jun. 23, 2022 to Extended European Search Report dated Dec. 6, 2021", 30 pgs.

* cited by examiner

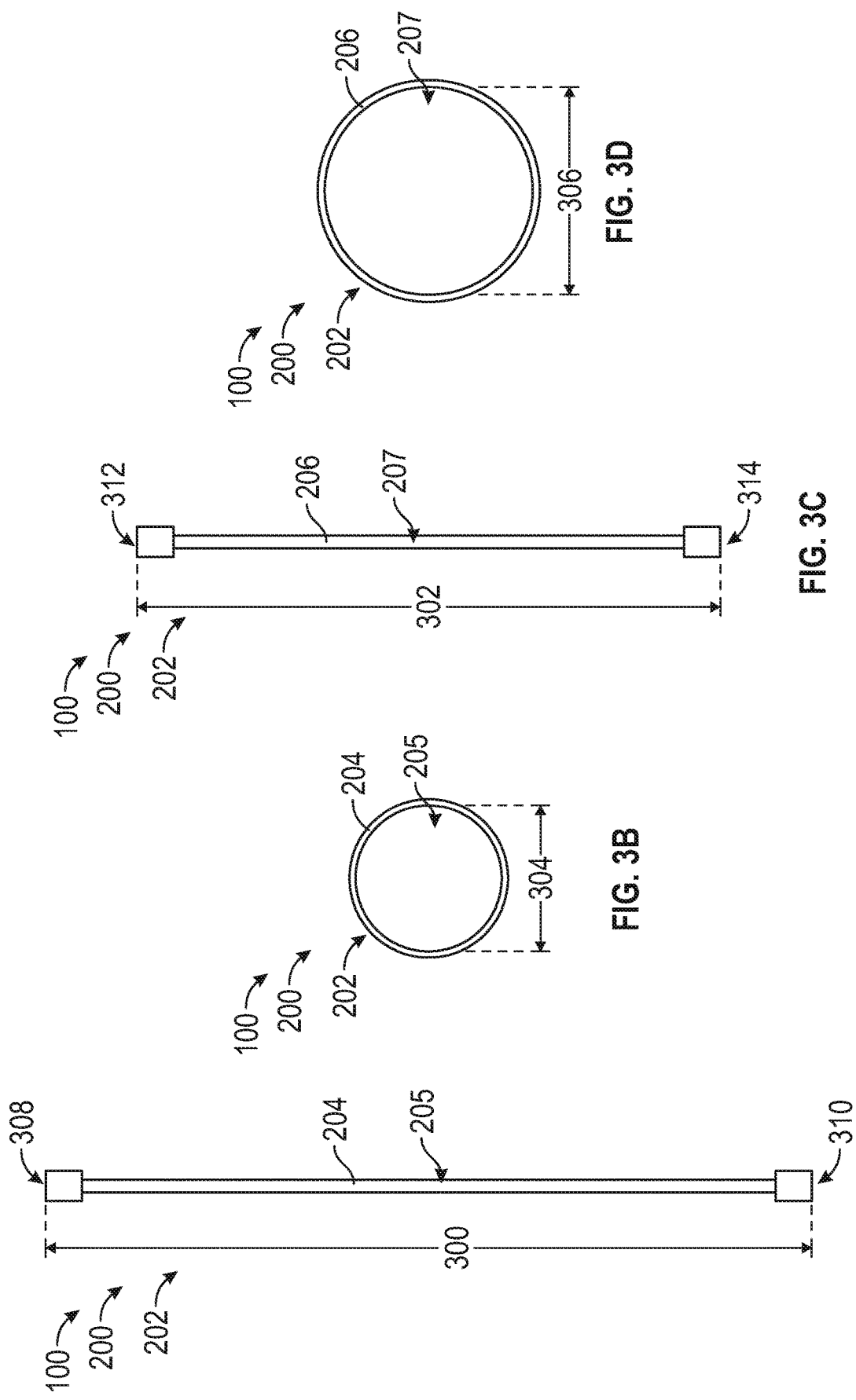

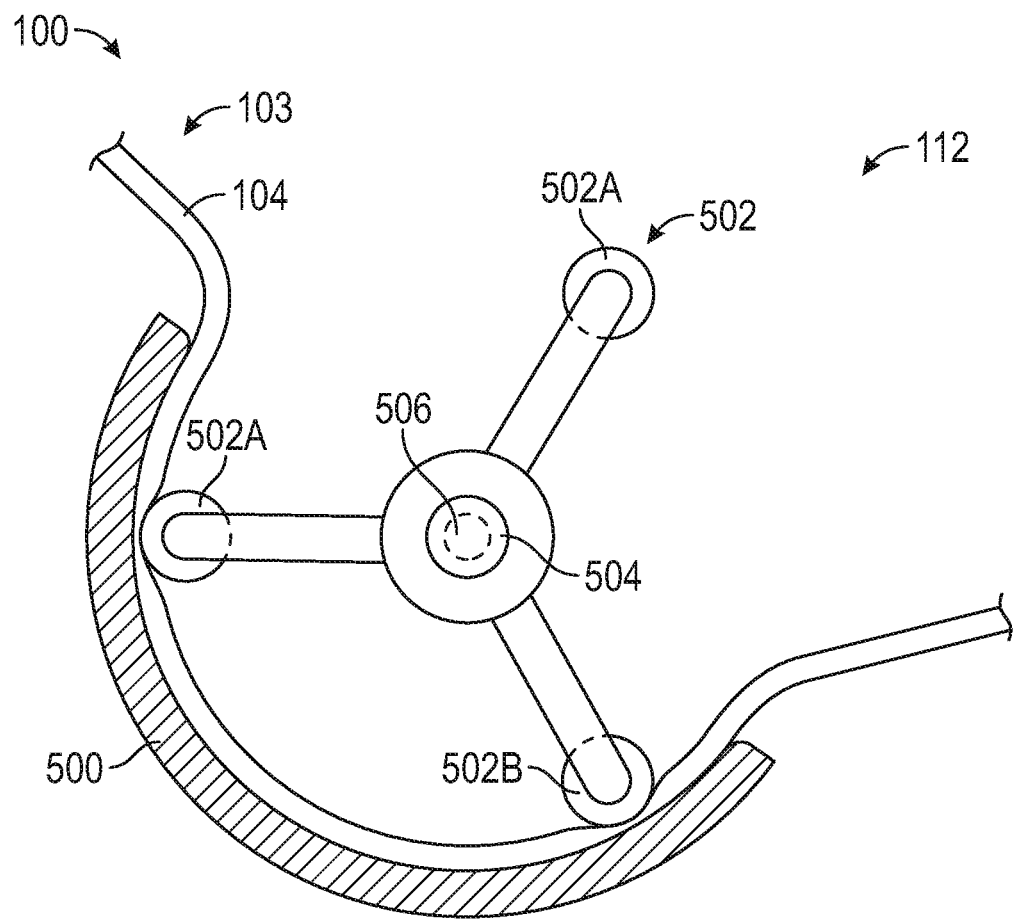
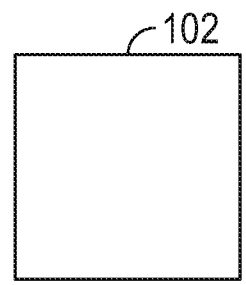
FIG. 5

NEONATAL AND PEDIATRIC BLOOD FILTRATION SYSTEM

CLAIM OF PRIORITY

This is a U.S. National Stage Filing under 35 U.S.C. 371 from International Application No. PCT/US2020/024974, filed on Mar. 26, 2020, which patent application claims the benefit of priority of Lerner et al., U.S. Provisional Patent Application Ser. No. 62/823,913, titled "BLOOD FILTRATION SYSTEM FOR NEONATAL AND PEDIATRIC PATIENTS," filed on Mar. 26, 2019 which is hereby incorporated by reference herein in its entirety.

TECHNICAL FIELD

This document pertains generally, but not by way of limitation, to blood filtration systems, for example a continuous renal replacement therapy system.

BACKGROUND

A blood filtration system may remove blood from the blood stream (e.g., venous circulation) of a patient and separate plasma water and electrolytes from erythrocytes (e.g., red blood cells) and other blood constituents by means of a filter. The system may convey the plasma water to a reservoir (e.g., a bag) for disposal. The balance of the plasma water, the erythrocytes, and other blood constituents are returned to the patient's blood stream.

SUMMARY

The hematocrit value in a patient is a ratio of the red blood cell volume to the total volume of blood in a patient, where the total volume of blood includes the red blood cell volume and the volume of plasma (including, but not limited to water, proteins, and electrolytes) in the blood of the patient. In some examples, a patient experiencing congestive heart failure (or other medical conditions) may have excess plasma volume, and accordingly a reduced hematocrit value. For instance, the patient may have excess plasma water that correspondingly increases the plasma volume of the patient (and lowers the hematocrit value of the patient). A blood filtration system may reduce the amount of plasma constituents (e.g., water and/or electrolytes) in the blood of the patient, and accordingly increase the hematocrit value of the patient.

As plasma constituents (e.g., filtrate fluid, ultrafiltrate, or the like) are removed from the circulatory system of a patient with the blood filtration system, fluid that is located in the interstitial space (e.g., tissue fluid/edema/congestion) may enter back into the circulatory system, for instance according to starling forces. In an example, as the plasma constituents are removed from the circulatory system by the blood filtration system, fluid may diffuse from tissue of a patient, and back into the circulatory system of the patient, thus compensating (e.g., in whole or in part) for the plasma constituents removed by the blood filtration system.

The rate at which this tissue fluid flows back into the circulatory system is known as the plasma refill rate ("PRR"). The PRR depends on multiple factors, including (but not limited to) plasma oncotic pressure, plasma hydrostatic pressure, interstitial osmotic pressure, interstitial hydrostatic pressure, and pressure derived from skin turgidity and elasticity. Accordingly, the PRR may vary from patient to patient or in one patient as therapy proceeds. In some approaches, if the filtration rate for removing the plasma constituents exceeds the PRR, too much plasma fluid may be removed from the circulatory system for a given period of time, or in an absolute sense (e.g., by removing too many plasma constituents too quickly, or removing many plasma constituents as a whole).

In some examples, the blood filtration system may be used with a neonatal or pediatric patient. A total blood volume of a neonatal or pediatric patient may be less than a total blood volume of an adult patient (e.g., an intravascular volume of a child may be less than an intravascular volume of an adult). With neonatal or pediatric patients, the balance between filtration rate and PRR may be monitored because of the reduced total blood volume of neonatal or pediatric patients in comparison to the total blood volume of an adult. For example, removal of excessive blood volume from the intracorporeal (e.g., within a circulatory system of a patient) to extracorporeal circulation (e.g., a blood circuit, including a filter that removes plasma constituents from blood flowing in the blood circuit) may lead to hemodynamic instability of the patient. A neonatal or pediatric patient may be more susceptible to hemodynamic instability, for example due to a reduced total blood volume (e.g., in comparison to a total blood volume of an adult).

The present inventors have recognized, among other things, that a problem to be solved may include reducing extracorporeal circulatory volume (e.g., a fluid capacity of a blood circuit) for a blood circuit, for example a blood circuit for use with a neonatal or pediatric patient. The present subject matter may help provide a solution to this problem, such as by providing a variable-volume blood circuit. In an example, the variable-volume blood circuit may include a catheter configured for insertion into a blood stream of the patient. The variable-volume blood circuit may include a first withdrawal line configured to couple with the catheter and having a first fluid capacity. The variable-volume blood circuit may include a first return line configured to couple with the catheter and having a second fluid capacity. The variable-volume blood circuit may include a first filter configured to reduce an amount of one or more plasma constituents in blood flowing through the first filter. The first filter may provide a filtrate fluid including the plasma constituents. The first filter may have a third fluid capacity. The first withdrawal line and the return line may be configured to couple with the first filter.

The variable-volume blood circuit may include one or more of a second withdrawal line, a second return line, or a second filter. The second withdrawal line may have a fourth fluid capacity. The second withdrawal line may be interchangeable with the first withdrawal line, for instance to change a total fluid capacity of the variable-volume blood circuit. The second return line may have a fifth fluid capacity. The second return line may be interchangeable with the first return line, for example to change the total fluid capacity of the variable-volume blood circuit. The second filter may have a sixth fluid capacity. The second filter may be interchangeable with the first filter, for instance to change the total fluid capacity of the variable-volume blood circuit.

The variable-volume blood circuit may facilitate a reduction in an extracorporeal (e.g., external to a patient) blood volume, for example to reduce occurrence of hemodynamic instability of a neonatal or pediatric patient. The variable-volume blood circuit may facilitate customizing the total fluid capacity of the variable-volume blood circuit, for example to allow the total fluid capacity of the variable-volume blood circuit to correspond to a total blood volume of a patient. Accordingly, the variable-volume blood circuit may enhance the safety, efficacy, or the like of the blood filtration system, for instance by reducing occurrence of hemodynamic instability in a patient.

In another example, an infusion pump may provide an infusion fluid to a blood circuit (e.g., the variable-volume blood circuit, or the like). Thus, the infusion pump may be coupled to the blood filtration system. For instance, the infusion pump may pump the infusion fluid to an infusion port in communication with the blood circuit. The infusion pump may be external to the blood filtration system. In an example, the blood filtration system includes a controller, and the controller is not in communication with the infusion pump. Accordingly, the controller may not be in communication with the infusion pump. For instance, the infusion pump may be operated by an infusion pump controller that is different than the controller for the blood filtration system.

The present inventors have recognized, among other things, that a problem to be solved may include monitoring operation of the infusion pump that is external to the blood filtration system. The present subject matter may help provide a solution to this problem, such as by providing a blood filtration system that may include a fluid characteristic sensor. The fluid characteristic sensor may be in fluidic communication with the infusion port. The fluid characteristic sensor may measure one or more of pressure or flow rate of the infusion fluid pumped by the infusion pump. The fluid characteristic sensor may be in communication with the controller for the blood filtration system, and the controller may monitor the fluid characteristic sensor, for example to determine a change in one or more of the pressure or flow rate of the infusion fluid. Accordingly, the blood filtration system may monitor operation of the infusion pump that is external to the blood filtration system (e.g., with the controller for the blood filtration system not in communication with the infusion pump).

In some approaches, the infusion pump that is external to the blood filtration system may not be in communication with the controller, and accordingly the controller may not modulate a speed of the infusion pump. For instance, the controller for the blood filtration system may be unable to control a flow rate of the infusion fluid pumped into the infusion port. As described herein, the controller for the blood filtration system may monitor operation of the infusion pump that is external to the blood filtration system. The blood filtration system may change a filtration rate of removing plasma constituents from blood of a patient based on changes in operation of the infusion pump.

In an example, the blood filtration system may include a variable-speed filtration pump that extracts a filtrate fluid from a filter, for instance a filter included in a blood circuit. The filter may reduce an amount of one or more plasma constituents in blood flowing through the filter. The filter may provide the filtrate fluid including the filtered plasma constituents, for example at a filtrate fluid port. The variable-speed filtration pump may extract the filtrate fluid from the filter. Modulating a speed of the variable-speed filtration pump may change the filtration rate of removing plasma constituents from blood of a patient. The controller may modulate (e.g., adjust, change, vary, alter, or the like) a speed of the variable-speed filtration pump (e.g., to change the filtration rate) based on a change in one or more of the pressure or flow rate of the infusion fluid pumped by the infusion pump. For example, the controller may reduce a speed of the variable-speed filtration pump based on a reduction in flow rate of the infusion fluid pumped by the infusion pump that is external to the blood filtration system. The controller may increase a speed of the variable-speed filtration pump (and according increase the filtration rate) based on an increase in flow rate of the infusion fluid pumped by the infusion pump. The controller may stop the variable-speed filtration pump if the flow of the infusion fluid is stopped. Accordingly, the blood filtration system may enhance the safety of therapy conducted with the blood filtration system, for example by decreasing occurrences of hemodynamic instability in a patient (e.g., due to a mismatch between filtration rate and a rate of infusion fluid pumped into the infusion port). For instance, the controller may stop the filtrate pump, and accordingly the blood filtration system may stop removing plasma constituents from blood of the patient if the flow of infusion fluid into the infusion port is stopped.

In some examples, the blood filtration system includes a variable-speed peristaltic pump. The peristaltic pump may include one or more rollers, and the one or more rollers may engage with a portion of the blood circuit to pump (e.g., push, circulate, cause a flow of, or the like) fluid within the blood circuit. For example, the peristaltic pump may facilitate pumping fluid in (or pumping fluid through), for example, one or more of a withdrawal line, a filter, or a return line. The present inventors have recognized, among other things, that a problem to be solved may include pulsatile pressure changes in the blood circuit corresponding to the one or more rollers engaging with the blood circuit.

In an example, the engagement of the one or more rollers with the blood circuit may cause the pulsatile pressure changes in the blood circuit. For instance, the one or more rollers may cyclically engage with the blood circuit during operation of the variable-speed peristaltic pump. In an example, as a first roller engages with the blood circuit, the pressure in the blood circuit may increase. The first roller may slidingly engage with the blood circuit (e.g., a withdrawal line), for example to push fluid through the blood circuit. The first roller may disengage from the blood circuit, and the pressure in the blood circuit may decrease when the roller disengages from the blood circuit.

The present subject matter may help provide a solution to this problem, such as by modulating a speed of the variable-speed peristaltic pump. The controller of the blood filtration system may modulate a speed of the peristaltic pump to adjust the speed of the peristaltic pump, for example when the one or more rollers are proximate to the blood circuit. Adjusting the speed of the peristaltic pump may reduce pulsatile pressure changes in the pressure circuit. For instance, the controller may reduce the speed of the peristaltic pump when the roller engages with the blood circuit. The controller may reduce the speed of the peristaltic pump prior to the roller engaging with the blood circuit. The reduction in speed of the peristaltic pump may slow the roller, for example to reduce a force applied to the blood circuit by the roller when the roller engages with the blood circuit. The adjustment in speed of the peristaltic pump may change a speed of the roller, for example to reduce a force applied to the blood circuit by the roller when the roller engages with the blood circuit. Accordingly, the blood filtration system may reduce pulsatile pressure changes in the blood circuit, for instance pulsatile pressure changes in the blood circuit corresponding to the one or more rollers engaging with the blood circuit.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3A shows a side view of an example of first withdrawal line extension.

FIG. 3B shows a side view of an example of a second withdrawal line extension.

FIG. 3C shows a cross-sectional view of the first withdrawal line extension of FIG. 3A.

FIG. 3D shows a cross-sectional view of the second withdrawal line extension of FIG. 3B.

FIG. 5 shows a schematic view of an example of a blood pump.

DETAILED DESCRIPTION

Figure 1:
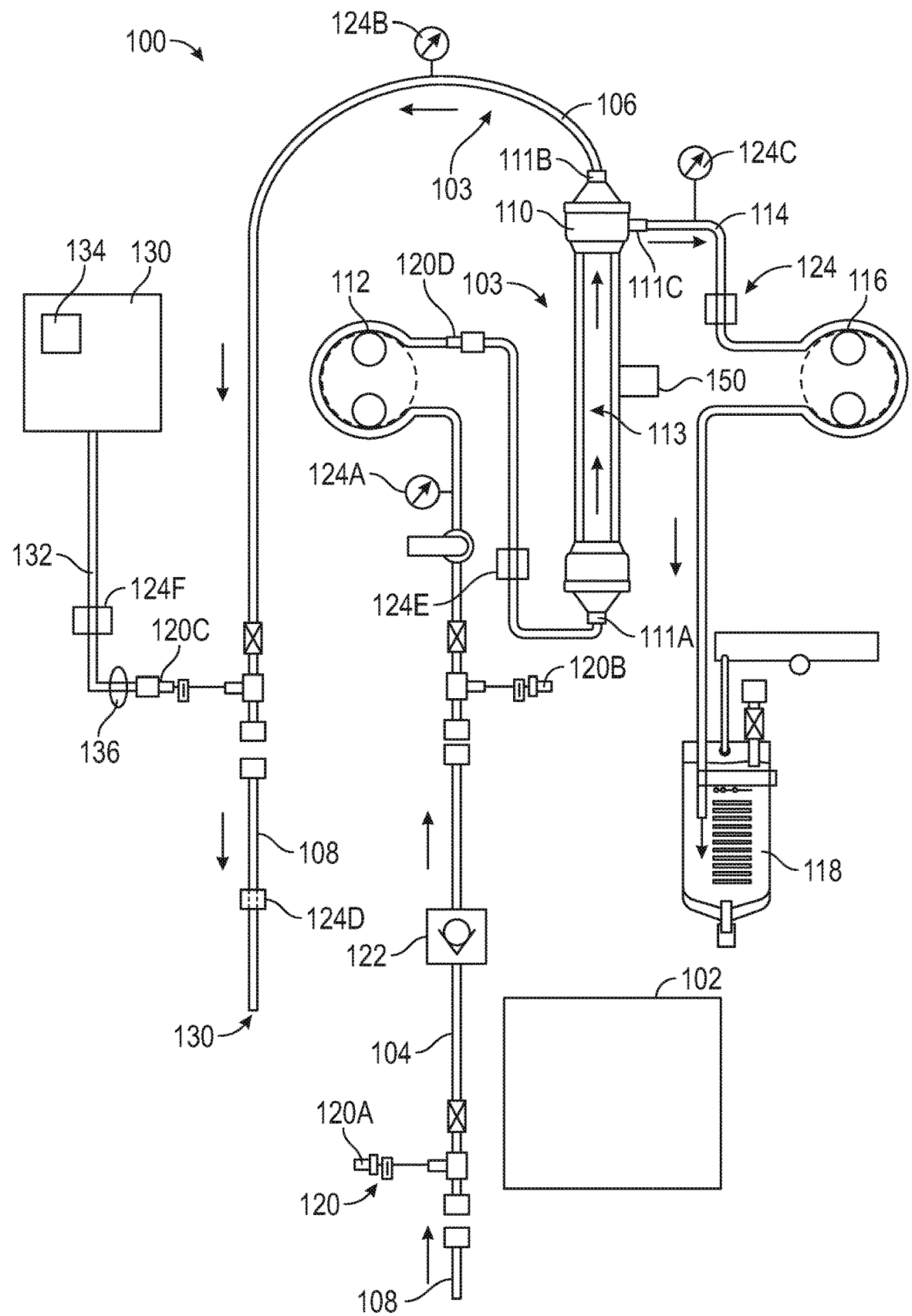
FIG. 1 shows a schematic view of an example of a blood filtration system.

FIG. 1 shows a schematic view of an example of a first blood filtration system 100. The blood filtration system 100 may reduce one or more plasma constituents (e.g., water, proteins, electrolytes, or the like) in blood of a patient. The blood filtration system 100 may include a controller 102. The controller 102 may include processing circuitry, for instance an integrated circuit. As described herein, the controller 102 may be configured to control one or more components of the blood filtrations system 100.

The blood filtration system 100 may include a blood circuit 103. In an example, the blood circuit 103 may include a withdrawal line 104, and may include a return line 106. The lines 104, 106 may couple with a catheter 108, and the lines 104, 106 may transmit blood within the blood filtration system 100. In an example, the catheter 108 may be inserted into a blood stream of the patient, for instance the catheter 108 may be inserted into a basilic vein, cephalic vein, brachial vein, the axillary vein, the subclavian vein, the brachiocephalic vein, or the like. Blood may flow into the catheter 108, into the withdrawal line 104, through other components of the system 100, through the return line 106, into the catheter 108, and back into the blood stream of the patient. The line 104 may be separate from the line 106. The lines 104, 106 may be in communication with the catheter 108. For example, the catheter 108 may include one or more lumens, for example a withdrawal lumen in communication with the line 104 and an infusion lumen in communication with the line 106.

The lines 104, 106 may couple with a filter 110, for instance the lines 104, 106 may include one or more fittings (e.g., connectors 212, shown in FIG. 2) that facilitate coupling the lines 104, 106 with the filter 110. In an example, the withdrawal line 104 may couple with a filter inlet port 111A, and the return line 106 may couple with a filter outlet port 111B. The filter 110 may reduce an amount of one or more plasma constituents (e.g., water, electrolytes, or the like) in blood flowing through the filter 110. The filter 110 may provide a filtrate fluid including the one or more plasma constituents. As described herein, blood may flow through the lines 104, 106 to and from the catheter 108. The lines 104, 106 may be coupled with the filter 110 and blood may flow from the withdrawal line 104, through the filter 110, and into the return line 106. As described in greater detail herein, the filter 110 may have a base filter fluid capacity 113.

The blood filtration system may include a blood pump 112, and the blood pump 112 may be configured to pump (e.g., convey, drive, push, or the like) blood through the blood filtration system 100. In an example, the blood pump 112 may be a peristaltic pump, and the blood pump 112 may engage with the withdrawal line 104 to pump blood through the withdrawal line 104 and into the filter 110. The controller 102 may be configured to operate the blood pump 112 to vary a speed of the blood pump 112 and accordingly vary the flow rate of blood through the blood filtration system 100 (e.g., the withdrawal line 104, the filter 110, the return line 106, or the like).

Referring again to FIG. 1, the blood filtration system 100 may include a filtration line 114 and a filtration pump 116. The filtration line 114 may be configured to couple with the filter 110 (e.g., with a fitting), for instance the filtration line 114 may couple with a filtrate fluid port 111C. The filter 110 may be configured to transmit the filtrate fluid (including one or more plasma constituents) to extracted by the filter 110 to the filtrate fluid port 111C.

The filtration pump 116 may pump extracted filtrate fluid from the filter 110, and into a filtrate fluid reservoir 118 (e.g., a bag, container, bladder, or the like). In some examples, the filtration pump 116 may be a peristaltic pump that engages with the filtration line 114 to pump the filtrate fluid through the filtration line 114. The controller 102 may be configured to vary a speed of the filtration pump 116 and accordingly vary the flow rate of filtrate fluid through the blood filtrate system 100 (e.g., the filtration line 114).

In some examples, the blood filtration system 100 may include one or more access ports 120, for instance a first access port 120A, a second access port 120B, and a third access port 120C. The access ports 120 may facilitate the extraction of blood from the blood filtration system 100, or injection of substances (e.g., a blood thinner, for instance heparin or the like) into the blood within the blood filtration system 100. In an example, the access ports 120A, 120B may be in communication with the withdrawal line 104, and the access port 120C may be in communication with the return line 106.

A valve 122 (e.g., a mechanical check valve, or electronically controlled valve) may be positioned between the access ports 120A, 120B, and the valves 122 may be configured to allow blood to flow unidirectionally within the withdrawal line 104 (e.g., flowing from the catheter 108 to the filter 110). In this example, a substance may be injected into the withdrawal line 104 at the access port 120B, and blood may be withdrawn from the access port 120A. Because the valve 122 facilitates unidirectional flow within the withdrawal line 104, the blood including the substance will not be withdrawn from the access port 120A, for instance because the access port 120A is upstream of the access port 120B). In an example, heparin may be infused into the access port 120B and blood is drawn from the access port 120A to measure blood clotting time parameters of a patient. Because the blood is drawn from the access port 120A, the withdrawn blood does not include heparin, and the blood clotting time parameter determination is not affected by the heparin injection at the access port 120B. Accordingly, the performance of blood filtration system 100 is thereby improved.

As shown in FIG. 1, the blood filtration system 100 may include one or more sensors 124 (e.g., transducer, accelerometer, or the like), for instance a first sensor 124A, a sensor 124B, and a sensor 124C. The first sensor 124A may measure (e.g., determine, calculate, obtain, provide, or the like) the pressure within the withdrawal line 104, the second sensor 124B may measure the pressure within the return line 106, and the third sensor 124C may measure the pressure within the filtration line 114. The sensors 124 may include a fourth sensor 124D (e.g., a position sensor, or the like) and a fifth sensor 124E (e.g., blood flow rate, or the like), and the sensor 124E may measure the blood flow rate through the system 100 (e.g., a component of the blood circuit 103, for example the withdrawal line 104).

The sensors 124 may include a gas detector that detects a discontinuity in flow of liquid through the blood circuit 103. For example, the sensor 124E (or the sensor 124F) may be a gas detector, and the sensor 124E may detect air or other gases in the blood circuit 103 (or the infusion line 132). For instance, the sensor 124E may be located between the blood pump 112 and the filter 110 and the sensor 124E may provide a signal to the controller 102 if the sensor 124E detects a discontinuity in flow of liquid (e.g., blood, filtrate fluid, infusion fluid, or the like) in the blood circuit 103. The controller 102 may stop one or more of the blood pump 112 or the filtration pump 116 if then sensor 124E detects a discontinuity in flow of liquid in the blood circuit 103. Accordingly, the blood filtration system 100 may inhibit gas (e.g., an air bubble, or the like) from entering vasculature of a patient.

An infusion pump 130 may pump infusion fluid into a patient. The infusion fluid may include saline, heparin, electrolytes, or the like. The infusion pump 130 may pump infusion fluid into the blood circuit 103. For example, the infusion pump 130 may be in communication with the one or more access ports 120, for instance with an infusion line 132. In an example, the infusion line 132 is coupled to the access port 120C. Accordingly, the access port 120C (or other ones of the access ports 120) may be an infusion port. The infusion pump 130 may be in fluidic communication with the blood circuit 103. For example, the infusion pump 130 may pump the infusion fluid into the infusion line 132 and into the port 120B. The infusion line 132 may be in fluidic communication with the withdrawal line 104. The infusion line 132 may be in fluidic communication with the return line 106.

The infusion pump 130 may be external to (e.g., not included in, separate from, distinct from, or the like) the blood filtration system 100. For instance, the infusion pump 130 may not be modulated by the controller 102 of the blood filtration system 100. In an example, the controller 102 may not be in communication with the infusion pump 130. Accordingly, the controller 102 may be unable to control operation of the infusion pump 130. For instance, the controller 102 may be unable to control a speed of the infusion pump 130. In an example, the infusion pump 130 includes an infusion pump controller 134 that controls operation of the infusion pump 130. The infusion pump controller 134 may be separate from the controller 102 for the blood filtration system 100. The controller 102 may not be in communication with the infusion pump controller 134.

The blood filtration system 100 may facilitate maintenance of hemodynamic stability of a patient. For instance, the blood filtration system 100 may cooperate with the infusion pump 130 that is external to the blood filtration system 100 to remove one or more plasma constituents form blood of a patient while maintaining hemodynamic stability of a patient. As described herein, the filtration pump 116 may pump extracted filtrate fluid from the filter 110. The infusion pump 130 may pump infusion fluid into the blood circuit 103, for example to replace a specified quantity of (e.g., a portion of, or an entirety of, or the like) the filtrate fluid extracted from the filter 110. Replacing the filtrate fluid with the infusion fluid may facilitate clearance of one or more plasma constituents from blood of a patient. For instance, the filtrate fluid may include water, electrolytes, and urea. The infusion fluid may include water and electrolytes. The infusion fluid may not include urea. Replacing the filtrate fluid with the infusion fluid may facilitate clearance of plasma constituents (e.g., urea, or the like) because the plasma constituents are removed in the filtrate fluid, and the plasma constituents may not be replaced by the infusion fluid. Replacing the filtrate fluid with the infusion fluid may facilitate maintenance of hemodynamic stability of the patient because the infusion fluid replaces the water and electrolytes extracted by the filtration pump 116. Accordingly, operation of the blood filtration system 100 (and the infusion pump 130) may facilitate removal of plasma constituents while maintaining hemodynamic stability of a patient.

The blood filtration system 100 may monitor the infusion pump 130, for example with a fluid characteristic sensor 124F. The fluid characteristic sensor may be in fluidic communication with an infusion port, for instance the third access port 120C or a fourth access port 120D. The fluid characteristic sensor 124F may measure characteristics of fluid, for example pressure of the infusion fluid. In an example, the sensor 124F may measure pressure at the access port 120C or measure pressure in the infusion line 132. The fluid characteristic sensor 124F may measure a flow rate of infusion fluid pumped by the infusion pump 130. For instance, the sensor 124F may measure a flow rate of infusion fluid flowing through the port 120C. The sensor 124F may measure a flow rate of infusion fluid flowing in the infusion line 132.

The fluid characteristic sensor 124F may be in communication with the controller 102 of the blood filtration system 100. For instance, sensor 124F may transmit an electrical signal corresponding to a measured pressure (or flow rate) to the controller 102. The controller may monitor the fluid characteristic sensor 124F, for example to determine a change in pressure of the infusion fluid pumped by the infusion pump 130. The controller 102 may determine a change in flow rate of the infusion fluid pumped by the infusion pump 130, for instance by monitoring the flow rate of the infusion fluid with the sensor 124F.

Monitoring the infusion pump 130 with the blood filtration system 100 may facilitate maintenance of hemodynamic stability of a patient. Because the infusion pump 130 may be external to the blood filtration system 100, the blood filtration system 100 may be unable to control the operation of the infusion pump 130. Accordingly, the infusion pump 130 may operate independently of the blood filtration system 100. For instance, the infusion pump 130 may pump infusion fluid into the blood circuit 103 when the filtration pump 116 is not extracting filtrate fluid from the filter 110. Accordingly, the infusion pump 130 may continue pumping infusion fluid while the blood filtration system 100 is not removing plasma constituents from blood of the patient. The continued pumping of infusion fluid by the infusion pump while the filtration pump 116 is not extracting filtrate fluid may cause hemodynamic instability in a patient (e.g., by continuing to add water to a patient with the infusion pump 130 without removing water from the patient with the blood filtration system 100). Conversely, extraction of filtrate fluid by the filtration pump 116 without pumping infusion fluid may lead to hemodynamic instability, for instance because plasma constituents are removed by the blood filtration system 100 without replacing the plasma constituents with the infusion fluid.

As described herein, monitoring the infusion pump 130 may facilitate maintenance of hemodynamic stability of a patient. In an example, the controller 102 of the blood filtration system 100 may modulate a speed of the variable-speed filtration pump 116 based on a change in pressure of the infusion fluid pumped by the infusion pump 130. The controller 102 of the blood filtration system 100 may modulate a speed of the variable-speed filtration pump 116 based on a change in flow rate of the infusion fluid pumped by the infusion pump 130. For instance, the controller 102 may monitor the sensor 124F and determine that the flow rate of the infusion fluid has decreased. The controller 102 may decrease the speed of the filtration pump 116 based on the decrease in flow rate of the infusion fluid pumped by the infusion pump 130.

The controller 102 may compare the measured fluid characteristics of the infusion fluid (e.g., pressure, flow rate, or the like) to an infusion fluid characteristic threshold (e.g., limit, bound, maximum, minimum, or the like). For example, if pressure in the infusion line 132 exceeds (e.g., decreases below, increases above, transgresses, or the like) the infusion fluid characteristic threshold, the controller 102 may generate a notification (e.g., by transmitting a signal to a speaker that generates an auditory alert). The controller 102 may modulate a speed of the filtration pump 116 (e.g., to adjust a flow rate through the filtration pump 116) based on the comparison of the measured fluid characteristics of the infusion fluid to the infusion fluid characteristic threshold. The controller 102 may modulate a speed of the filtration pump 116 based on the comparison of a change in the measured fluid characteristics of the infusion fluid, for instance when the infusion fluid characteristic threshold is exceeded. For instance, the controller 102 may stop the filtration pump 116 if the flow rate of infusion pump is below the infusion fluid characteristic threshold. The controller 102 may increase the speed of the filtration pump 116 if the flow rate of the infusion fluid increases beyond the infusion fluid characteristic threshold. Accordingly, monitoring the infusion pump 130 may facilitate maintenance of hemodynamic stability of a patient, for instance by inhibiting removal of filtrate fluid when infusion fluid is not replacing the filtrate fluid extracted by the filtration pump 116.

The controller 102 may compare the measured fluid characteristics of the blood circuit 103 to a circuit fluid characteristic threshold, for instance to determine if the blood circuit 103 is leaking, over-pressured, exceeding a maximum flow rate, or the like. For instance, one or more of the sensors 124 may measure fluid characteristics (e.g., one or more of pressure, flow rate, or the like) of the blood circuit 103. For instance, the first sensor 124A may measure the pressure within the withdrawal line 104, the second sensor 124B may measure the pressure within the return line 106. The controller 102 may monitor the sensors 124A, 124B and compare the measured fluid characteristics in the lines 104, 106 to the circuit fluid characteristic threshold. In an example, if the measured fluid characteristics in the lines 104, 106 exceeds the circuit fluid characteristic threshold, the controller 102 may stop the blood pump 112. The controller 102 may stop the filtration pump 116 if the measured fluid characteristics in the lines 104, 106 exceeds the circuit fluid characteristic threshold, the controller 102 may stop the blood pump 112. The controller 102 may provide a notification if the measured fluid characteristics in the lines 104, 106 exceeds the circuit fluid characteristic threshold.

The blood filtration system 100 may include an infusion valve 136. The infusion valve 136 may selectively inhibit flow of the infusion fluid into the blood circuit 103. For instance, the infusion valve 136 may be in communication with the controller 102, and the controller 102 may modulate the infusion valve 136. The infusion valve 136 may include (but is not limited to) a ball valve, pinch valve (e.g., a valve that pinches the infusion line 132 closed), check valve, or the like Because the infusion pump 130 is external to the blood filtration system 100, the controller 102 may not operate the infusion pump 130. Accordingly, the controller 102 may modulate the infusion valve 136 to change the flow of infusion fluid through the infusion valve 136. For instance, the controller 102 may modulate the flow the infusion valve 136 to stop flow of infusion fluid if the sensors 124 (e.g., sensor 124E, or the like) detect a discontinuity in flow of liquid in the blood circuit 103.

In an example, the controller 102 may modulate the infusion valve 136 to inhibit (e.g., stop, reduce, limit, or the like) flow of infusion fluid through the valve 136. The controller 102 may modulate the infusion valve 136 to allow flow of infusion fluid through the infusion valve 136 (e.g., to allow full flow, partial flow, or the like). The controller 102 may modulate the infusion valve 136 based on the operation of the filtration pump 116 (or the blood pump 112). For instance, the controller 102 may modulate the infusion valve 136 to inhibit flow of infusion fluid if the filtration pump 116 exceeds a speed threshold. In an example, the controller 102 may modulate the infusion valve 136 to stop flow of infusion fluid into the blood circuit 103 if the filtration pump 116 is stopped (e.g., when the filtration pump 116 is not extracting filtrate fluid from the filter 110). The controller may modulate the valve 136 if the measured fluid characteristics in the lines 104, 106 exceeds the circuit fluid characteristic threshold.

As described herein, the controller 102 may monitor operation of the infusion pump 130, for example by monitor a change in pressure, or a change in flow rate, of infusion fluid pumped by the infusion pump 130. The controller 102 may modulate the infusion valve 136 based on a comparison of the fluid characteristics of the infusion fluid to the infusion fluid characteristic threshold. For example, the controller 102 may modulate the infusion valve 136 to inhibit flow of the infusion fluid if the flow rate of infusion fluid exceeds a specified flow rate (e.g., corresponding to the infusion fluid characteristic threshold). Accordingly, the blood filtration system 100 may control the flow of infusion fluid into the blood circuit 103 with the infusion pump 130 being external to the blood filtration system 100 (e.g., because the controller 102 may be unable to operate the infusion pump 130). Thus, the blood filtration system 100 may facilitate maintenance of hemodynamic stability of a patient.

Figure 2A:
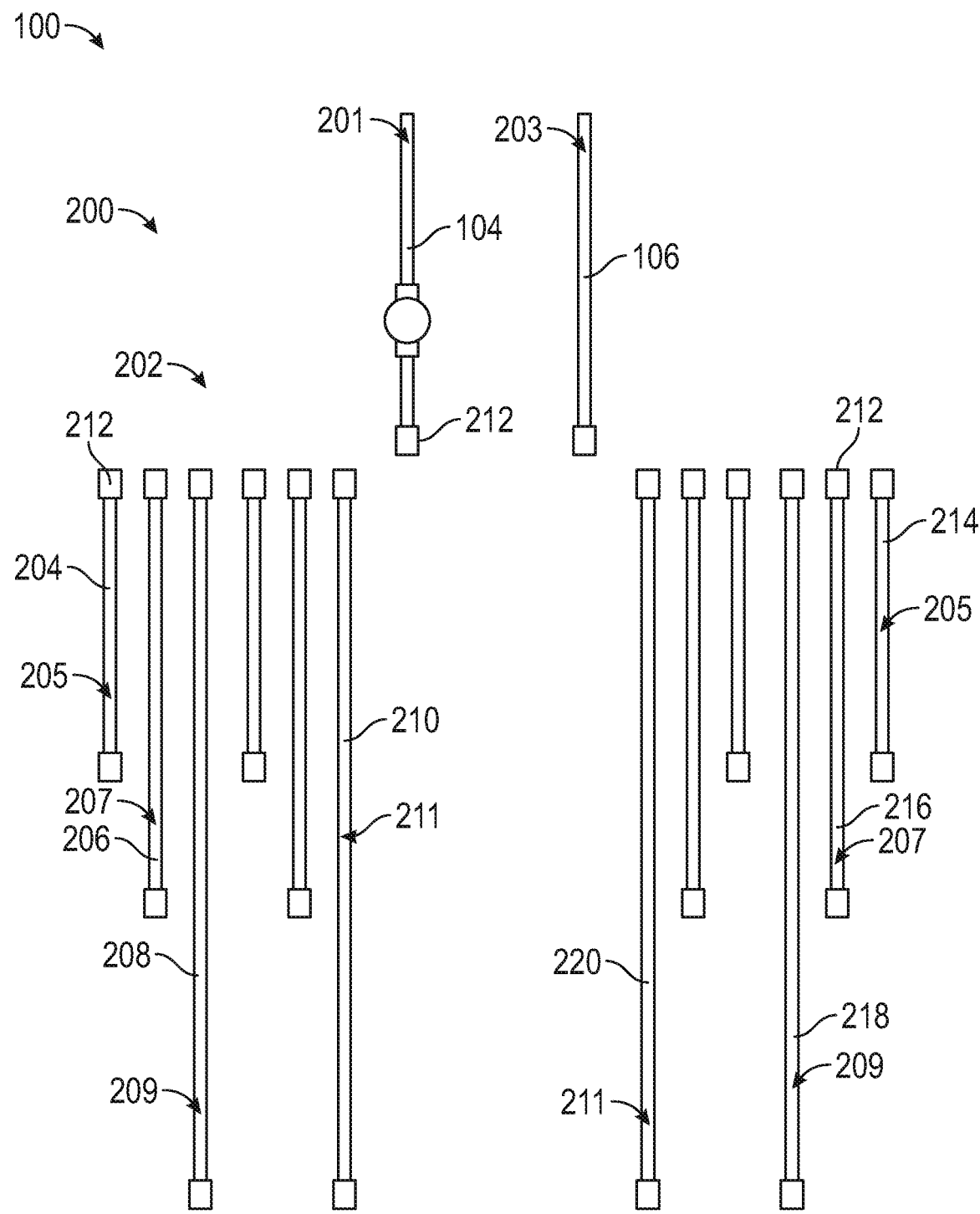
FIG. 2A shows a schematic view of an example of a portion of a variable-volume blood circuit.

FIG. 2A shows a schematic view of an example of a portion of a variable-volume blood circuit 200. The blood filtration system 100 may include the variable-volume blood circuit 200. The variable-volume blood circuit 200 may be similar to (or may include) the blood circuit 103. For example, the variable-volume blood circuit 200 may include the withdrawal line 104 and may include the return line 106. The variable-volume blood circuit 200 may include one or more circuit extensions 202 that facilitate a change in a total fluid capacity (e.g., volume, size, quantity, or the like) for the variable-volume blood circuit 200. The total fluid capacity of the variable-volume blood circuit 200 may include a sum of fluid capacities of components of the variable-volume blood circuit 200 (e.g., one or more of line 104, line 106, catheter 108, filter 110, extensions 202, or the like). In an example, the withdrawal line 104 may have a first base fluid capacity 201 (e.g., 5 milliliters, 10 milliliters, 25 milliliters, or the like). The return line 106 may have a base return line fluid capacity 203. The filter 110 may have a base filter fluid capacity 113 (shown in FIG. 1). The sum of the base withdrawal line fluid capacity 201, the base return line fluid capacity 203, and the base filter fluid capacity 113 may correspond to the total fluid capacity of the variable-volume blood circuit 200.

The circuit extensions 202 may be interchangeable. The circuit extensions 202 may couple with the withdrawal line 104 to change the total fluid capacity of the variable-volume blood circuit 200. The circuit extensions 202 may couple with the return line 106 to change the total fluid capacity of the variable-volume blood circuit 200. For instance, the variable-volume blood circuit 200 may include one or more of a first withdrawal extension 204, a second withdrawal extension 206, a third withdrawal extension 208, or a fourth withdrawal extension 210. The extension 204 may have a first extension fluid capacity 205 (e.g., 1 milliliter, 6 milliliters, 25 milliliters, or the like). The extension 206 may have a second extension fluid capacity 207 (e.g., 2 milliliters, 7 milliliters, 30 milliliters, or the like). The extension 208 may have a third extension fluid capacity 209 (e.g., 3 milliliters, 8 milliliters, 40 milliliters, or the like). The extension 210 may have a fourth extension fluid capacity 211 (e.g., 4 milliliters, 9 milliliters, 47 milliliters, or the like).

The variable-volume blood circuit 200 may include one or more connectors 212 (e.g., fittings, adaptors, couplers, or the like) that facilitate coupling the extensions 202 to the lines 104, 106 (or a filter, for example the filter 110, shown in FIG. 1). The extensions 204, 206, 208, 210 may couple with the withdrawal line 104 to change the total fluid capacity of the variable-volume blood circuit 200. The connectors 212 may facilitate interchanging the extensions 202 with each other to change the total fluid capacity of the variable-volume blood circuit 200.

For instance, the connectors 212 may facilitate coupling the extension 204 with the withdrawal line 104 and provide the variable-volume blood circuit 200 with a first total fluid capacity (e.g., 10 milliliters, 15 milliliters, 23 milliliters, or the like). The connectors 212 may facilitate coupling the extension 206 with the withdrawal line to provide the variable-volume blood circuit 200 with a second total fluid capacity (e.g., 12 milliliters, 18 milliliters, 50 milliliters, or the like). Accordingly, the extensions 202 are interchangeable with each other, for example to provide the variable-volume blood circuit 200 with a plurality of total fluid capacities. In an example, the variable-volume blood circuit 200 may have the first total fluid capacity, the second total fluid capacity, a third total fluid capacity, a fourth total fluid capacity, or the like.

The extensions 202 may be combined together (or interchanged with each other) to change the total fluid capacity of the variable-volume blood circuit 200 (e.g., by coupling the extension 202 with the withdrawal line 104 or by coupling the extension 206 with the withdrawal line 104). Accordingly, the variable-volume blood circuit 200 facilitate limiting an extracorporeal volume of blood in the blood circuit 200. For instance, the total fluid capacity of the blood circuit 200 may be established at the first total fluid capacity for use with an infant. The total fluid capacity of the blood circuit 200 may be established at the second total fluid capacity for use with an adult. The infant may have a limited quantity of blood for the blood circuit 200. The total fluid capacity may be established to meet the needs of a patient, for example to facilitate maintenance of hemodynamic stability of the patient.

The circuit extensions 202 may couple with the return line 106, for example to change the total fluid capacity of the variable-volume blood circuit 200. In an example, the variable-volume blood circuit 200 may include one or more of a first return extension 214, a second return extension 216, a third return extension 218, or a fourth return extension 220. The first return extension 214 may have the first extension fluid capacity 205. The second return extension 216 may have the second extension fluid capacity 207. The third return extension 218 may have the third extension fluid capacity 209. The fourth return extension 220 may have the fourth extension fluid capacity 211. The extension fluid capacities of the return extensions 214, 216, 218, 220 may be different than the extension fluid capacities of the withdrawal extensions 204, 206, 208, 210.

Figure 2B:
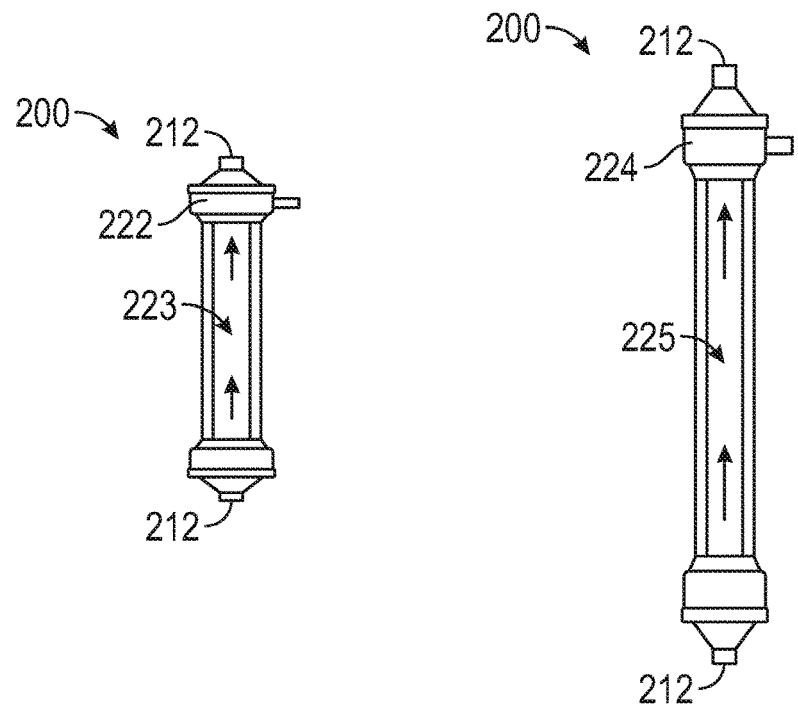
FIG. 2B shows another schematic view of the variable-volume blood circuit of FIG. 2A.

FIG. 2B shows another schematic view of the variable-volume blood circuit 200. As described herein, the variable-volume blood circuit 200 may include the filter 110 (shown in FIG. 1). The filter 110 may be a first filter having a first filter fluid capacity (e.g., 10 milliliters, or the like). The variable-volume blood circuit may include a second filter 222, and the second filter may have a second filter fluid capacity 223 (e.g., 20 milliliters, or the like). The variable-volume blood circuit 200 may include a third filter 224, and the third filter 224 may have a third filter fluid capacity 225 (e.g., 30 milliliters, or the like).

In an example, the second filter fluid capacity 223 may differ from the third filter fluid capacity 225, for instance to facilitate a change in the total fluid capacity of the variable-volume blood circuit 200. For instance, the connectors 212 may facilitate interchanging of the second filter 222 with the third filter 224 in the variable-volume blood circuit 200. Accordingly, the interchangeability of components of the variable-volume blood circuit 200 facilitates changing the total fluid capacity of the variable-volume blood circuit 200.

Figure 2C:
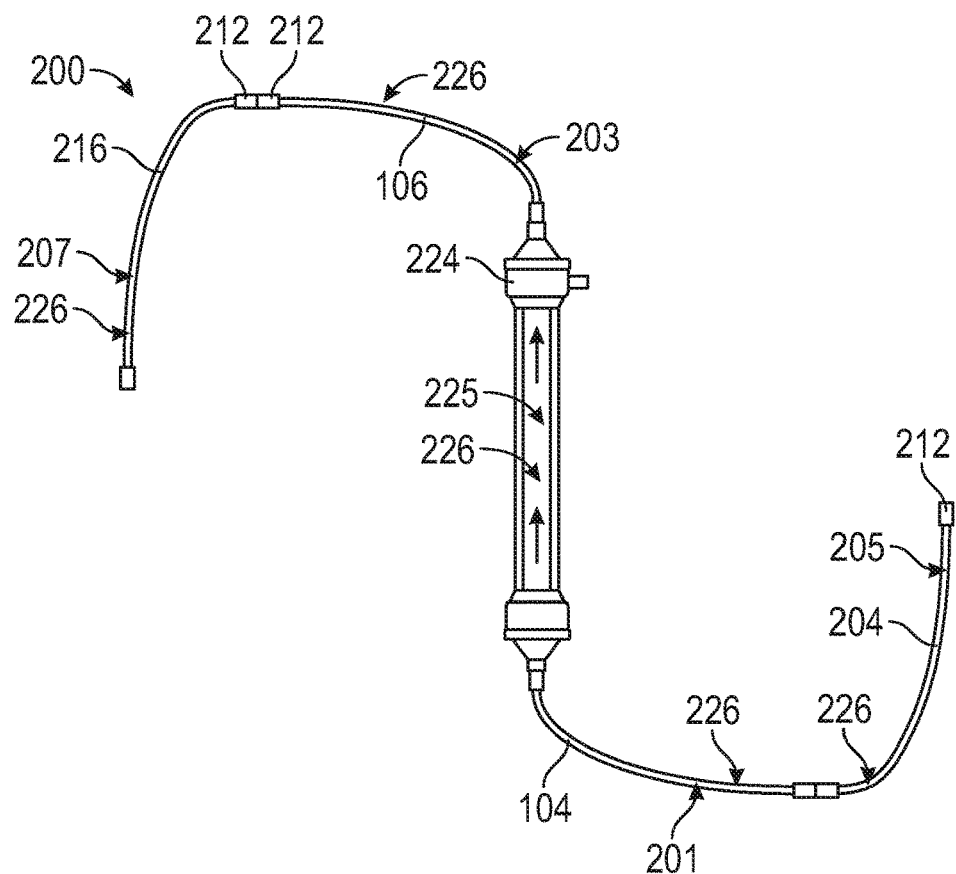
FIG. 2C shows yet another schematic view of the variable-volume blood circuit of FIG. 2A.

FIG. 2C shows yet another schematic view of the variable-volume blood circuit 200. As described herein, components of the variable-volume blood circuit 200 are interchangeable to change a total fluid capacity 226 of variable-volume blood circuit 200. For instance, the connectors 212 may facilitate coupling the extensions 202 with the withdrawal line 104. The connectors 212 may facilitate coupling the extensions 202 with the return line 106. The connectors 212 may facilitate coupling the lines 104, 106 with a filter, for example the filter 224. The connectors 212 may facilitate coupling the extensions 202 with a filter, for instance the filter 222 (shown in FIG. 2B).

The total fluid capacity 226 of the variable-volume blood circuit 200 may correspond to a sum of fluid capacities of components of the variable-volume blood circuit 200. For instance, the total fluid capacity 226 may include the fluid capacity 201 of the withdrawal line 104, the fluid capacity 205 of the extension 204, the fluid capacity 225 of the filter 224, the fluid capacity 203 of the return line 106, and the fluid capacity 207 of the extension 216. Interchanging of components of the variable-volume blood circuit 200 may change the total fluid capacity 226 of the variable-volume blood circuit 200. In an example, interchanging the filter 224 having the third filter fluid capacity 225 with the filter 222 having the second filter fluid capacity 223 (shown in FIG. 2B) may facilitate changing the total fluid capacity 226 of the variable-volume blood circuit 200.

A person having ordinary skill in the art will appreciate that the circuit extensions 202 may be included in the lines 104, 106. For instance, the lines 104, 106 may have varying lengths, dimensions, fluid capacities, or the like to facilitate a change in the total fluid capacity of the variable-volume blood circuit 200.

FIGS. 3A-3D show side and cross-sectional views of the first withdrawal extension 204 and the second withdrawal extension 206. As described herein, components of the variable-volume blood circuit 200 may be interchangeable, for example to change the total fluid capacity of the variable-volume blood circuit 200. In an example, the first withdrawal extension 204 may have the first fluid capacity 205, and the second withdrawal extension 206 may have the second fluid capacity 207. The difference between the fluid capacities 205, 207 may correspond to a change in dimensions of the withdrawal extensions 204, 206. For instance, the first withdrawal extension 204 may have a first length 300. The second withdrawal extension 206 may have a second length 302. The difference between the first length 300 and the second length 302 may correspond to the difference in the fluid capacities 205, 207 of the withdrawal extensions 204, 206. For instance, the difference between the lengths 300, 302 may correspond to a difference in volume between the extensions 204, 206.

The difference between the fluid capacities 205, 207 of the withdrawal extensions 204, 206 may correspond to a change in internal dimensions of the withdrawal extensions 204, 206. For example, the first withdrawal extension 204 may have a first internal dimension 304 (e.g., an internal diameter, internal area, or the like). The second withdrawal extension 204 may have a second internal dimension 306. The difference between the first internal dimension 304 and the second internal dimension 306 may correspond to the difference in the fluid capacities 205, 207 of the withdrawal extensions 204, 206. For instance, the difference between the first internal dimension 304 and the second internal dimension 306 may correspond to a difference in volume between the extensions 204, 206.

As described herein, the controller 102 (shown in FIG. 1) may compare the measured fluid characteristics of the blood circuit 103 to the circuit fluid characteristic threshold, for example to determine if the blood circuit 103 is leaking. Similarly, the controller 102 (shown in FIG. 1) may compare the measured fluid characteristics of the variable-volume blood circuit 200 to the circuit fluid characteristic threshold. Because the components of the variable-volume blood circuit 200 are interchangeable (e.g., to change the total fluid capacity of the variable-volume blood circuit 200), the circuit fluid characteristic threshold may be adjusted to correspond to the components used in the variable-volume blood circuit 200.

In an example, the difference between the length 300 of the withdrawal extension 204 and the length 302 of the withdrawal extension 206 may correspond to a difference in fluid flow characteristics between the withdrawal extension 204 and the withdrawal extension 206 (or other ones of the extensions 202). For example, fluid flowing through the withdrawal extension 204 may have (or may experience) a first pressure differential between a first end 308 of the withdrawal extension 204 and a second end 310 of the withdrawal extension 204. Fluid flowing through the withdrawal extension 206 may have (or may experience) a second pressure differential between a first end 312 of the withdrawal extension 206 and a second end 310 of the withdrawal extension 206.

The blood filtration system 100 may change one or more system parameters (e.g., the infusion fluid characteristic threshold, the circuit fluid characteristic threshold, or the like) based on which components of the variable-volume blood circuit 200 are used during therapy with the system 100. For instance, because the components of the variable-volume blood circuit 200 may have different fluid capacities, the blood filtration system 100 may adjust the system parameters to enhance accuracy (or precision) of the measured fluid characteristics of the blood circuit 200. The blood filtration system 100 may adjust the system parameters to enhance the operation of the system, for example by enhancing the capability of the system 100 to maintain hemodynamic stability of a patient. Adjusting the system parameters may ensure that the system parameters are accurate with respect to the components of the blood circuit 200 that are used during therapy. Thus, the blood filtration system 100 may tailor the system parameters based on which components of the variable-volume blood circuit 200 are used during therapy with the system 100.

In an example, the blood filtration system 100 may compensate for the difference in fluid flow characteristics of the extensions 202. The controller 102 may adjust the circuit fluid characteristic threshold to compensate for the difference between the first pressure differential of the extension 204 and the second pressure differential of the extension 206. For instance, the controller 102 may compare the measured fluid characteristics of the blood circuit 200 to a first circuit characteristic threshold when the first withdrawal extension 204 is used with the blood circuit 200 (e.g., when the extension 204 is coupled with the line 104). The controller 102 may compared the measured fluid characteristics of the blood circuit 200 to a second circuit characteristic threshold when the second withdrawal extension 204 is used with the blood circuit 200. Accordingly, the blood filtration system 100 may compensate for different fluid flow characteristics of the variable-volume blood circuit 200.

Similarly, the controller 102 may modulate the speed of the blood pump 112 based on which components (e.g., the extensions 202, or the like) of the variable-volume blood circuit 200 are used during therapy with the system 100. For example, the controller 102 may limit the speed of the blood pump 112 at a first flow rate (e.g., 10 milliliters per minute, or the like) when the first withdrawal extension 204 is used with the blood circuit 200. The controller 102 may limit the speed of the blood pump 112 at a second flow rate (e.g., 15 milliliters per minute, or the like) when the second withdrawal extension 206 is used with the blood circuit 200.

The controller 102 may modulate the speed of the filtration pump 116 based on which components (e.g., the filter 222 or the filter 224, shown in FIG. 2B, or the like) of the variable-volume blood circuit 200 are used during therapy with the system 100. For instance, the controller 102 may limit the speed of the filtration pump 116 at a first flow rate (e.g., 1 milliliter per minute, or the like) when the first withdrawal extension 204 is used with the blood circuit 200. The controller 102 may limit the speed of the filtration pump 116 at a second flow rate (e.g., 7 milliliters per minute, or the like) when the second withdrawal extension 206 is used with the blood circuit 200.

In some examples, fluid flow characteristics of the circuit extensions 202 may be normalized (e.g., made consistent, made equal, made uniform, or the like). Normalizing the fluid flow characteristics of the circuit extensions 202 may enhance the accuracy (or precision) of measuring fluid characteristics of the variable-volume blood circuit 200. For example, because the first pressure differential across the first withdrawal extension 204 is different than the second pressure differential across the second withdrawal extension 204, the pressure readings provided by the sensors 124 may be inaccurate (or imprecise). Normalizing the fluid flow characteristics of the circuit extensions may reduce the inaccuracies (or imprecision) of measuring the fluid characteristics of the variable-volume blood circuit 200.

For instance, the fluid flow characteristics of the first withdrawal line extension 204 may correspond to the fluid flow characteristics of the second withdrawal line extension 206 to normalize the fluid flow characteristics of the extensions 204, 206. In an example, a pressure differential across the first withdrawal line extension 204 may equal a pressure differential across the second withdrawal line extension 206. The pressure differential across the first withdrawal line extension 204 may be similar to the pressure differential across the second withdrawal line extension 206.

The fluid flow characteristics of the extensions 202 may be different based on dimensions of the extensions 202. In an example, the internal dimension 304 of the first withdrawal extension 204 and the internal dimension 306 of the second withdrawal extension 206 may be equal. The length 300 of the extension 204 may be different than the length 302 extension 206. Accordingly, the fluid flow characteristics of the extensions 204, 206 may be different, for example because the first pressure differential across the extension 204 may be different than the second pressure differential across the extension 206.

The fluid flow characteristics of the circuit extensions 202 may be normalized by varying dimensions of the circuit extensions 202. For example, the internal dimension 304 of the first withdrawal extension 204 may be varied to normalize the pressure differential across the first withdrawal extension 204 with the pressure differential across the second withdrawal extension 206.

In an example, the length 300 of the extension 204 may be different than the length 302 of the extension 206 (e.g., the extension 206 may be longer than the extension 204). Thus, the pressure differentials across the extensions 204, 206 may be different. The internal dimension 304 of the first withdrawal extension 204 may be different than the internal dimension 306 of the second withdrawal line extension 206 to normalize the fluid flow characteristics of the extensions 204, 206. For example, the internal dimension 306 of the extension 206 may be greater than the internal dimension 304 of the extension 204 (e.g., while the length 300 of the extension 204 is greater than the length 302 of the extension 206). Accordingly, the pressure differential across the extensions 204, 206 may be normalized. Thus, the extensions 202 may be normalized to enhance the accuracy (or precision) of measuring fluid flow characteristics in the variable-volume blood circuit 200. In an example, normalizing the fluid flow characteristics of the circuit extensions 202 may minimizing the adjustment of system parameters based on which components of the variable-volume blood circuit 200 are used during therapy with the blood filtration system 100.

Figure 4:
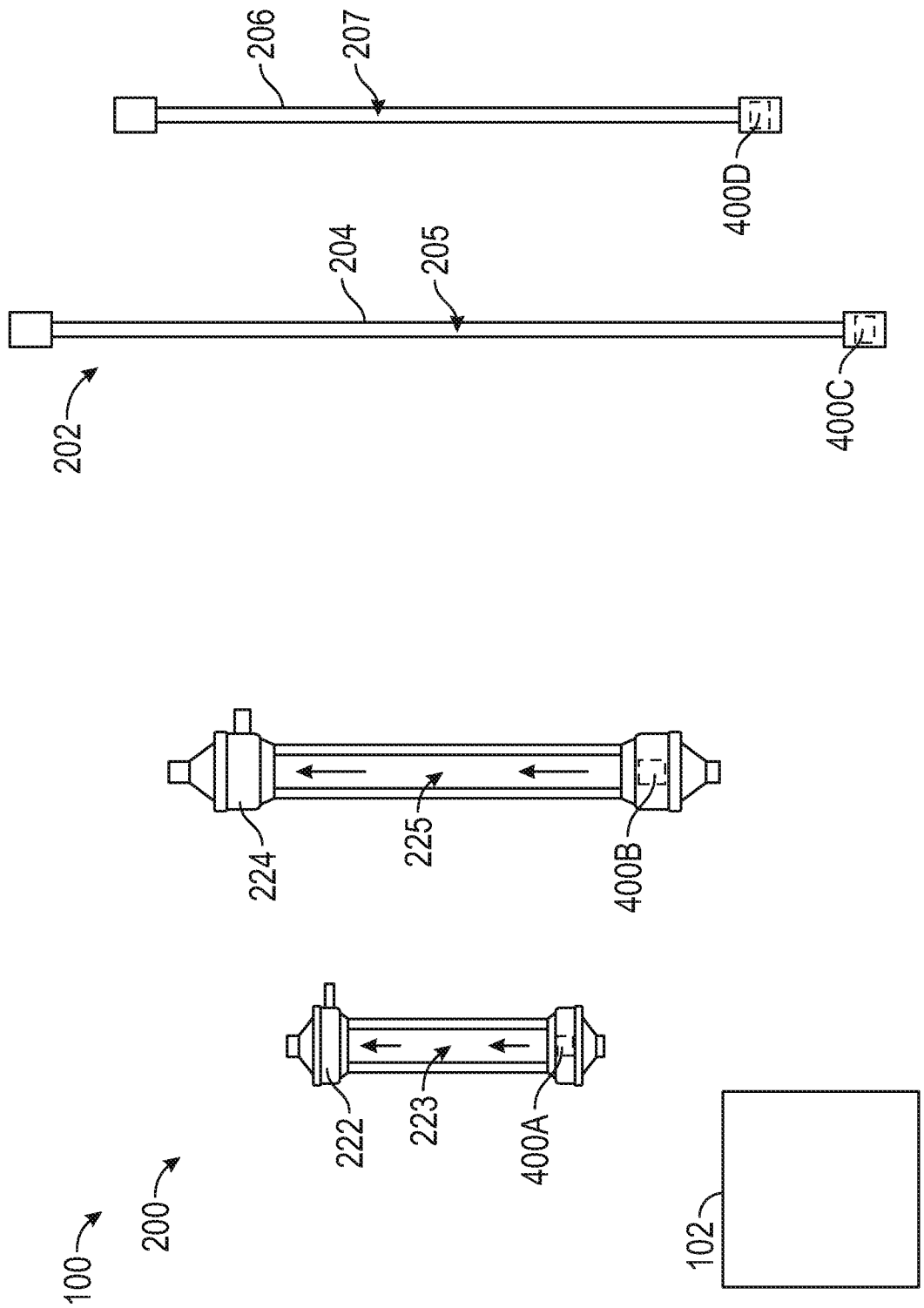
FIG. 4 shows a side view of the variable-volume blood circuit of FIGS. 2A-2C.

FIG. 4 shows a side view of the variable-volume blood circuit 200. The variable-volume blood circuit 200 may include one or more activation keys 400. The activation keys 400 may provide information to the blood filtration system 100 about the variable-volume blood circuit 200. For instance, the activation keys 400 may provide information about fluid capacities for components of the variable-volume blood circuit 200 (or the blood circuit 103, shown in FIG. 1).

The activation keys 400 may communicate with the controller 102, for example with a wired (e.g., with a cable, or the like) or a wireless connection (e.g., an RFID tag, or an IEEE 802.11 standard such as Bluetooth, or the like). The activation keys may provide the information about the variable-volume blood circuit 200 (or the blood circuit 103, shown in FIG. 1) to the controller 102. Accordingly, the blood filtration system 100 (e.g., the controller 102) may adjust system parameters of the blood filtration system 100, for example to enhance accuracy (or precision) of the measured fluid characteristics of the variable-volume blood circuit 200. In an example, the activation keys 400 may facilitate determining the total fluid capacity 226 (shown in FIG. 2C) of the variable-volume blood circuit 200 with the controller 102. The activation keys 400 may facilitate establishing the circuit fluid characteristic threshold, for example because the activation keys 400 provide fluid flow characteristics of the circuit extensions 202 to the controller 102. The controller 102 may limit the speed of the blood pump 112 (or the filtration pump 116) based on the information provided by the activation keys 400.

In an example, the second filter 222 may include a first activation key 400A, and the first activation key 400A may communicate with the controller 102 to provide the controller 102 with the second filter fluid capacity 223. The activation key 400A may provide fluid flow characteristics of the filter 222 to the controller 102. The third filter 224 may include a second activation key 400B, and the second activation key 400B may communicate with the controller 102 to provide the controller 102 with the third filter fluid capacity 225. The activation key 400B may provide fluid flow characteristics of the filter 224 to the controller 102. Accordingly, the blood filtration system 100 may adjust system parameters based on the information provided by the activation keys 400A, 400B.

The circuit extensions 202 may include the activation keys 400, and the activation keys may provide information about the circuit extensions 202. For instance, the first withdrawal extension 204 may include a third activation key 400C, and the third activation key may communicate with the controller 102 to provide the controller 102 with the first extension fluid capacity 205. The activation key 400C may provide fluid flow characteristics of the extension 204 to the controller 102. The second withdrawal extension 206 may include a fourth activation key 400D, and the fourth activation key may communicate with the controller 102 to provide the controller 102 with the first extension fluid capacity 205. The activation key 400D may provide fluid flow characteristics of the extension 206 to the controller 102. Accordingly, the blood filtration system 100 may adjust system parameters based on the information provided by the activation keys 400A, 400B.

FIG. 5 shows a schematic view of an example of the blood pump 112. Portions of the blood pump 112 may be hidden in FIG. 5 for clarity. The blood pump 112 may include a peristaltic pump. For instance, the blood pump 112 may include a pump housing 500. The blood pump 112 may include one or more rollers 502. For example, the blood pump 112 may include a first roller 502A, a second roller 502B, and may include a third roller 502C.

The one or more rollers 502 may engage with the blood circuit 103 (or the variable-volume blood circuit 200) to pump fluid through the blood circuit 103. For example, the withdrawal line 104 may be located partially within the blood pump 112. The withdrawal line may engage with the pump housing 500, and the withdrawal line 104 may be located between the rollers 502 and the pump housing 500. The rollers 502 may rotate about an axis 504, and the rollers 502 may cyclically engage with the withdrawal line 104 to pump fluid through the withdrawal line 104 (or other components of the blood circuit 103.

In an example, the rollers 502 may compress (e.g., squeeze, squish, press, indent, or the like) the withdrawal line 104 between the rollers 502 and the pump housing 500. The compression of the withdrawal line 104 may close (e.g., pinch, seal, or the like) the withdrawal line 104. The rollers 502 may slidingly engage with the withdrawal line 104, for example according to rotation of the rollers 502 about the axis 504. The sliding engagement with the withdrawal line 104 may pump fluid through the withdrawal line 104. For example, because the rollers 502 compress the withdrawal line 104, the rollers may push fluid through the withdrawal line 104 (or other components of the blood circuit 103) as the rollers 502 slidingly engage with the withdrawal line 104. Accordingly, operation of the blood pump 112 may pump fluid through the blood circuit 103.

The engagement of the rollers 502 with the blood circuit 103 may cause pulsatile pressure changes (or pulsatile flow changes) in the blood circuit 103. Similarly, the disengagement of the rollers 502 with the blood circuit 103 may cause pulsatile pressure changes in the blood circuit 103. In an example, the rotation of the rollers 502 about the axis 504 may cause the rollers 502 to cyclically engage (e.g., periodically engage, or the like) with the withdrawal line 104. For instance, the second roller 502B and the third roller 502C may be engage with the withdrawal line 104. The engagement of the rollers 502 may cause a pressure increase in the withdrawal line 104. Rotation of the rollers 502 about the axis 504 may cause the third roller 502C to disengage from the withdrawal line 104. The disengagement of the third roller 502C may cause pressure in the withdrawal line 104 to decrease. As the rollers 502 continue to rotate about the axis 504, the first roller 502A may engage with the withdrawal line 104, and cause pressure to increase in the withdrawal line 104. Accordingly, the cyclic engagement with the blood circuit 103 may cause the pulsatile pressure (or flow) changes in the blood circuit 103. The sensors 124 (shown in FIG. 1) may measure the pulsatile pressure changes in the blood circuit 103.

The pulsatile pressure changes may cause corresponding pulsatile changes in the flow of fluid in the blood circuit 103. Accordingly, reduce the pulsatile pressure changes in the blood circuit 103 may reduce pulsatile change in flow in the blood circuit 103. The pulsatile pressure changes may cause cavitation in the flow of liquid in the blood circuit 103 (e.g., the pulsatile pressure changes may generate gas in the flow of liquid in the blood circuit 103). Accordingly, reducing pulsatile pressure changes in the blood circuit 103 may reduce cavitation in the blood circuit 103. In an example, reducing pulsatile pressure changes in the blood circuit 103 may decrease instantaneous changes in pressure or flow rate of fluid in the blood circuit 103.

As described herein, pulsatile pressure changes in the blood circuit 103 may correspond to the rollers 502 engaging with (or disengaging from) the blood circuit 103. The controller 102 may modulate the speed of the blood pump 112 to reduce the pulsatile pressure changes in the blood circuit 103. For example, the controller 102 may adjust the speed of the peristaltic pump when the rollers 502 are proximate to the blood circuit 103. Adjusting the speed of the peristaltic pump when the rollers 502 are proximate to the blood circuit 103 may reduce pulsatile pressure changes in the blood circuit 103.

In an example, the controller 102 may be in communication with an encoder 506. The encoder 506 may provide an angular position of the rollers 502 to the controller 102. Accordingly, the controller 102 may determine when the rollers 502 are proximate the blood circuit 103 (e.g., prior to engagement with withdrawal line 104, prior to disengagement with the withdrawal line 104, or the like), for example based on the angular position of the rollers 502. The controller 102 may modulate the speed of the peristaltic pump based on the angular position of the rollers 502.

For instance, the controller 102 may decrease the speed of the speed of the blood pump 112 prior to the rollers 502 (e.g., the third roller 502C, or the like) disengaging from the blood circuit 103. The controller 102 may decrease the speed of the blood pump 112 prior to the rollers 502 engaging with the blood circuit 103. The controller 102 may increase the speed of the blood pump 112 when the rollers 502 are engaged with the blood circuit 103.

Figure 6:
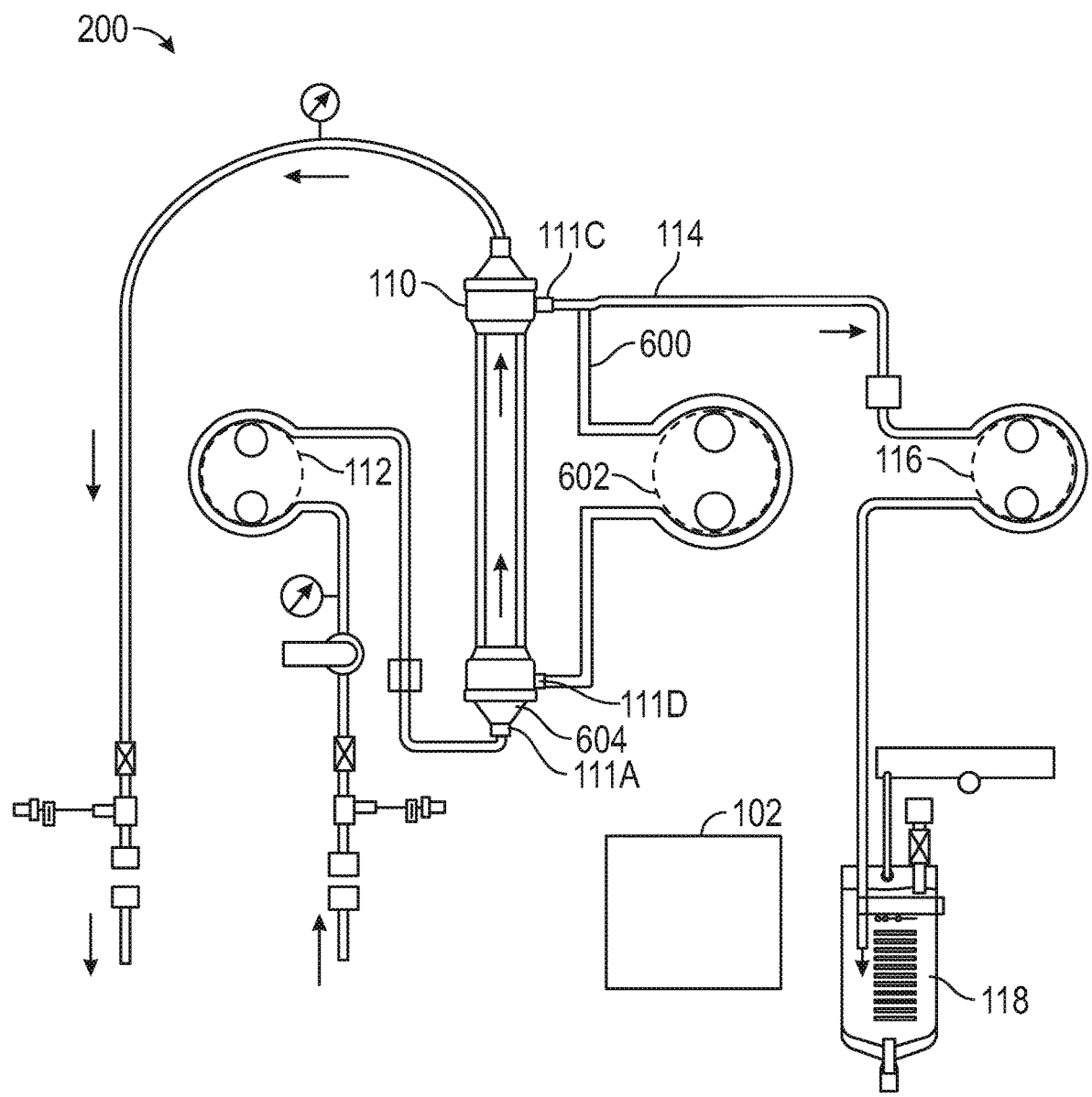
FIG. 6 shows a schematic view of another example of the blood filtration system.

FIG. 6 shows a schematic view of another example of the blood filtration system 100. The blood filtration system 100 may include, but is not limited to, the blood pump 112, the filter 110, the filtration line 114, and the filtration pump 116. The filtration system 100 may include a harvest fluid line 600, and may include a harvesting pump 602. The harvest fluid line 600 may be in communication with the filtrate fluid port 111C, for example, the harvest fluid line 600 may be coupled to the filtration line 114, and the harvest fluid line 600 may receive filtrate fluid from the filtration line 114.

In some examples, the filter 110 includes a harvesting port 111D. The harvesting port 111D may be configured to receive filtrate fluid. In an example, the harvest fluid line 600 may be coupled with the harvesting port 111D, and the harvesting port 111D may be in communication with the filtrate fluid port 111C through the harvest fluid line 600. The harvesting pump 602 may engage with the harvest fluid line 600 and may pump filtrate fluid from the filtrate fluid port 111C to the harvesting port 111D. The controller 102 may operate (e.g., activate, turn on, energize, provide a control signal to, provide an instruction, or the like) the harvesting pump 602 to extract filtrate fluid from a filtrate reservoir (e.g., the filtrate fluid port 111C, the filtration line 114, or the filtrate fluid reservoir 118) and inject the filtrate fluid into the harvesting port 111D to dilute the blood flowing through the filter.

Injecting filtrate fluid into the harvesting port 111D may mix filtrate fluid with blood entering the filter inlet port 111A, and accordingly dilute the blood with the filtrate fluid. In an example, diluting blood flowing through the filter 110 may decrease clotting in the filter 110. Diluting blood flowing through the filter 110 may enhance the performance of the filter 110, for example by increasing a length of time that the filter 110 may remove plasma constituents from blood of a patient.

In some examples, the harvesting port 111D may be included in (e.g., extends from, or is in communication with) a filter body 604 of the filter 110. In another example, the harvesting port 111D may be coupled with the filter inlet port 111A. Optionally, a one-way valve may be included between the filtrate fluid port 111C and the harvesting port 111D, for instance to inhibit blood flow within the harvest fluid line 210 while allowing filtrate fluid to flow from the filtrate fluid port 111C to the harvesting port 111D. As described in greater detail herein, the harvesting port 111D may provide filtrate fluid into the filter 1110, for example to dilute blood within the filter 110 and inhibit clotting of blood flowing through the filter 110.

Figure 7:
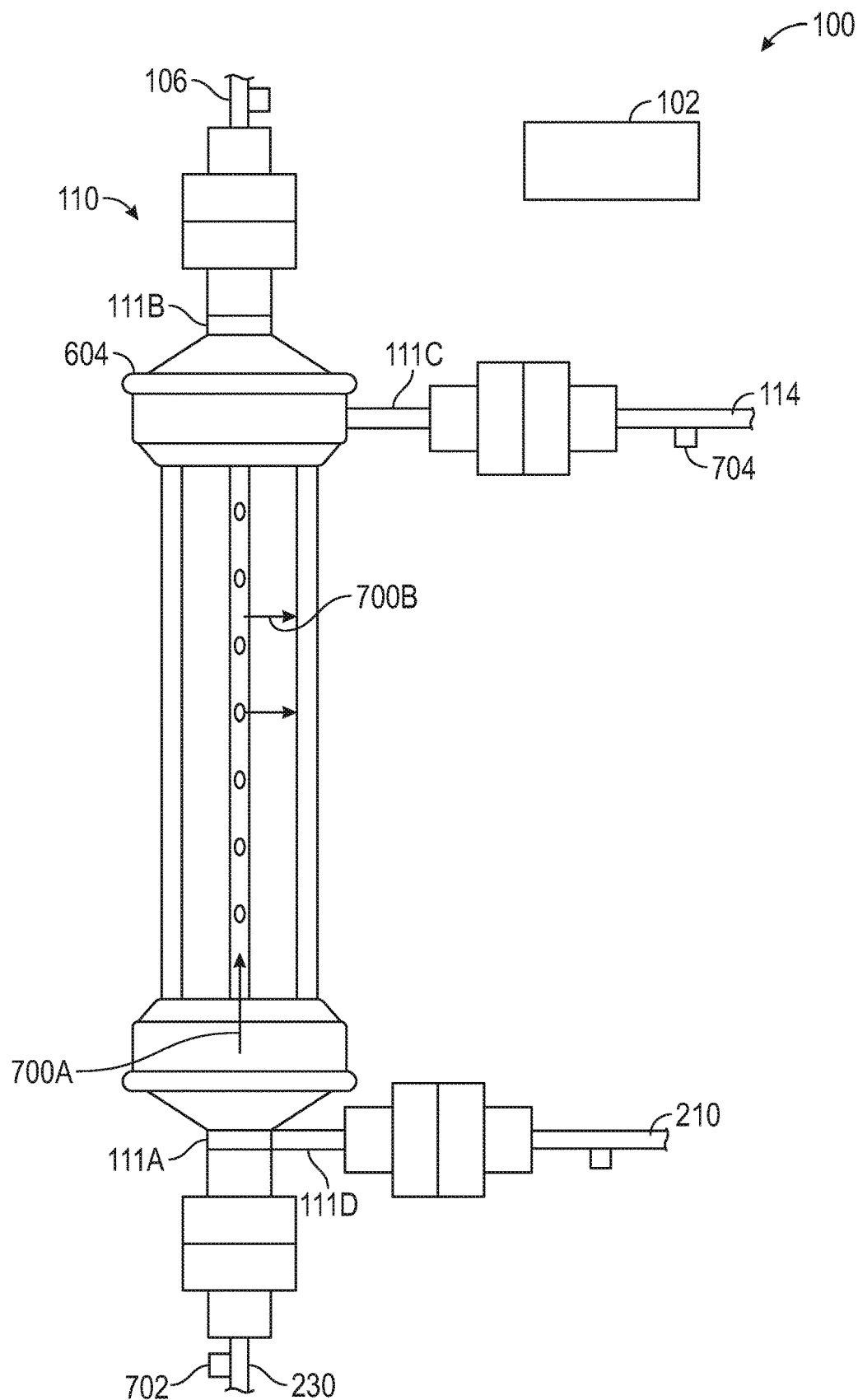
FIG. 7 shows a side view of a portion of a blood circuit.

FIG. 7 shows a side view of a portion of the blood circuit 103. The blood filtration system 100 may include the controller 102, and the controller 102 may determine one or more filter resistances of the filter 110. In an example, the filter 110 may have a longitudinal resistance characteristic, and the longitudinal resistance characteristic may include the resistance of the flow of a fluid (e.g., blood) through a length of the filter 110, for instance as denoted by arrow 700A. In one example, the controller 102 may determine the longitudinal filter resistance characteristic by determining the pressure at an inlet pressure sensor 702 that is in communication with the inlet port 111A of the filter 110.

As the filter 110 filters blood, the filter 110 may become clogged, for instance due to clotting in the filter 110. As the filter 110 becomes clogged, the longitudinal filter resistance of the filter 110 increases, because the clogged filter increases the amount of force necessary to pump blood through the filter 110. Accordingly, the pressure at the inlet pressure sensor 702 may increase.

The controller 102 may compare longitudinal filter resistance characteristic to a filter resistance threshold, for instance a first filter resistance threshold, and determine if the longitudinal filter resistance characteristic exceeds the first filter resistance threshold. In this example, when the longitudinal filter resistance exceeds (e.g., is greater than) the first filter resistance threshold, the controller 102 may operate (e.g., with a control signal, instruction, or the like) a harvesting pump (e.g., the harvesting pump 602 shown in FIG. 6). Operating the harvesting pump may inject a fluid (e.g., filtrate fluid, saline, heparin, or the like) into the port 111D, and introduce the fluid into blood flowing into the filter 110. For instance, injecting the filtrate fluid into the port 111D may reduce the longitudinal filter resistance characteristic, for instance by diluting blood clotted in the filter 110. The controller 102 may be configured to operate the harvesting pump and stop injecting filtrate fluid into the port 111D when the longitudinal filter resistance characteristic exceeds (e.g., is less than) a second filter resistance threshold. Accordingly, the performance of the blood filtration system 100 is improved because a lifetime of the filter 110 may be extended by reducing clogging of the filter 110.

The filter 110 may have a transverse resistance characteristic, and the transverse resistance characteristic may include the resistance of the flow of a fluid (e.g., filtrate fluid) through a thickness of the filter 110, for instance as denoted by arrow 700B. In an example, the controller 102 may determine the transverse filter resistance characteristic by determining the pressure at a filtration pressure sensor 704 that is in communication with the filtrate fluid port 111C of the filter 110. As the filter 110 filters blood, the filter 110 may become clogged, for instance due to clotting in the filter 110. As the filter 110 becomes clogged, the transverse filter resistance of the filter 110 increases, because the clogged filter increases the amount of force necessary to extract filtrate fluid from the filter 110 (e.g., with the filtration pump 116 shown in FIG. 1). Accordingly, the pressure at the inlet pressure sensor 704 may increase.

The controller 102 may compare the transverse resistance characteristic to a filter resistance threshold, for instance a first filter resistance threshold, and determine if the transverse resistance characteristic exceeds (e.g., is greater than) the first filter resistance threshold. In this example, when the transverse filter resistance exceeds the first filter resistance threshold, the controller 102 may operate (e.g., with a control signal, instruction, or the like) a harvesting pump (e.g., the harvesting pump 602 shown in FIG. 6). Operating the harvesting pump may inject filtrate fluid into the port 111D, and dilute the blood flowing into the filter 110. Injecting the filtrate fluid into the port 111D may reduce the transverse filter resistance characteristic, for instance by diluting blood clotted in the filter 110. The controller 102 may operate the harvesting pump and stop injecting filtrate fluid into the port 111D, for example when the transverse filter resistance characteristic exceeds (e.g., is less than) a second filter resistance threshold. Accordingly, the performance of the blood filtration system 100 is improved because a lifetime of the filter 110 may be extended by reducing clogging of the filter 110.

The controller 102 may compare a filter resistance characteristic (e.g., a transverse filter resistance, longitudinal filter resistance, or the like) to a first filter resistance threshold when the variable-volume blood circuit has a first total fluid capacity. The controller 102 may compare a filter resistance characteristic to a second filter resistance threshold when the variable-volume blood circuit 200 has a second total fluid capacity. Accordingly, performance of the filtration system 100 may be enhanced, for instance to reduce clotting in one or more of the filter 110 (shown in FIG. 1), the second filter 222, or the third filter 224 (shown in FIG. 2).

Figure 8:
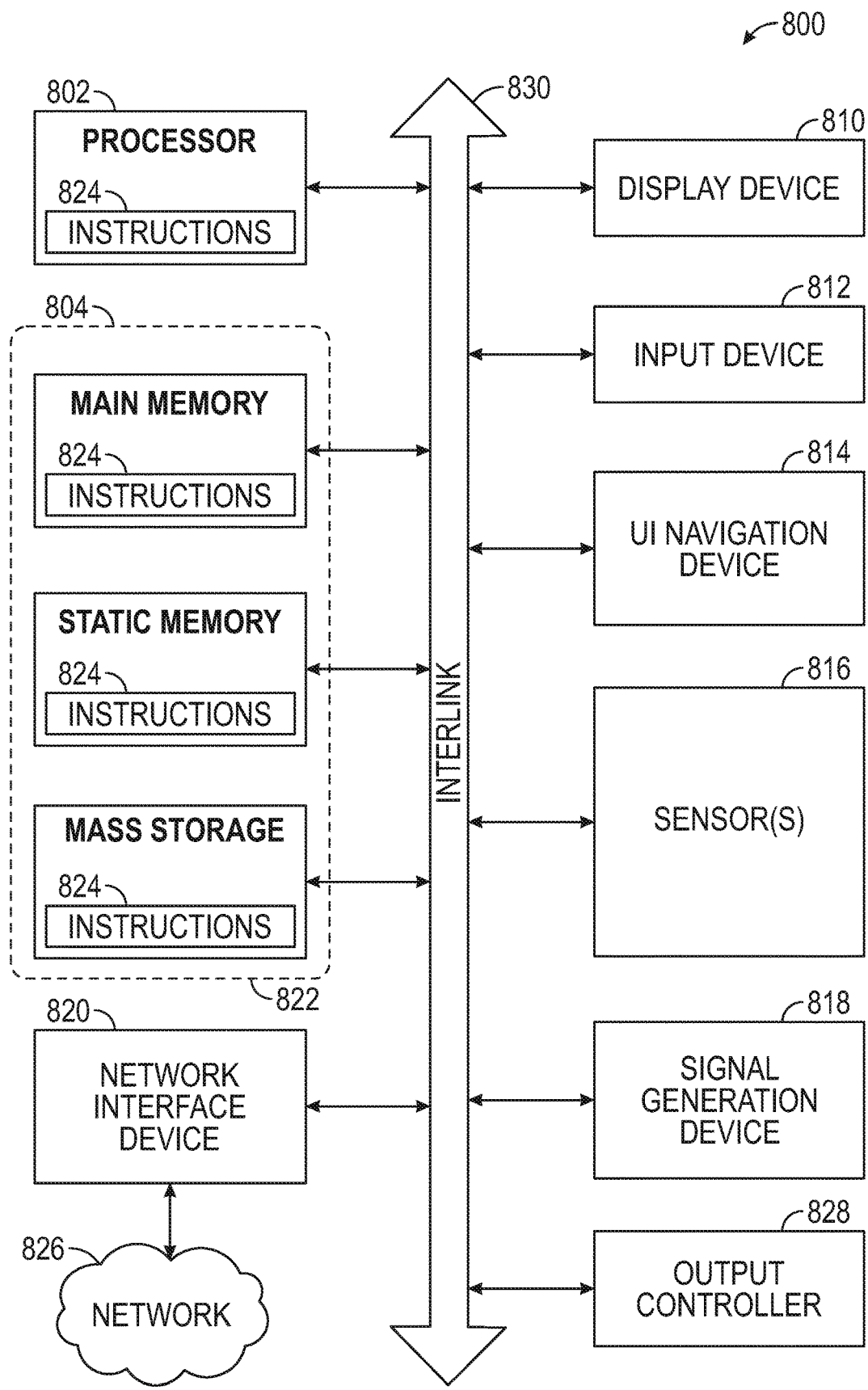
FIG. 8 shows a block diagram of an example machine.

FIG. 8 shows a block diagram of an example machine 800 upon which any one or more of the techniques (e.g., methodologies) discussed herein may perform. The machine 800 may include the controller 102. Examples, as described herein, may include, or may operate by, logic or a number of components, or mechanisms in the machine 800. Circuitry (e.g., processing circuitry) is a collection of circuits implemented in tangible entities of the machine 800 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 800 follow.

In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed) network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 800 may include a hardware processor 802 (e.g., a central processing unit (CPU), a graphics processing unit (GPU), a hardware processor core, or any combination thereof), a main memory 804, a static memory (e.g., memory or storage for firmware, microcode, a basic-input-output (BIOS), unified extensible firmware interface (UEFI), etc.) 806, and mass storage 808 (e.g., hard drive, tape drive, flash storage, or other block devices) some or all of which may communicate with each other via an interlink (e.g., bus) 830. The machine 800 may further include a display unit 810, an alphanumeric input device 812 (e.g., a keyboard), and a user interface (UI) navigation device 814 (e.g., a mouse). In an example, the display unit 810, input device 812 and UI navigation device 814 may be a touch screen display. The machine 800 may additionally include a storage device (e.g., drive unit) 808, a signal generation device 818 (e.g., a speaker), a network interface device 820, and one or more sensors 816, such as a global positioning system (GPS) sensor, compass, accelerometer, or other sensor. The machine 800 may include an output controller 828, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 802, the main memory 804, the static memory 806, or the mass storage 808 may be, or include, a machine-readable medium 822 on which is stored one or more sets of data structures or instructions 824 (e.g., software) embodying or utilized by any one or more of the techniques or functions described herein. The instructions 824 may also reside, completely or at least partially, within any of registers of the processor 802, the main memory 804, the static memory 806, or the mass storage 808 during execution thereof by the machine 800. In an example, one or any combination of the hardware processor 802, the main memory 804, the static memory 806, or the mass storage 808 may constitute the machine-readable media 822. While the machine-readable medium 822 is illustrated as a single medium, the term "machine-readable medium" may include a single medium or multiple media (e.g., a centralized or distributed database, and/or associated caches and servers) configured to store the one or more instructions 824.

The term "machine-readable medium" may include any medium that is capable of storing, encoding, or carrying instructions for execution by the machine 800 and that cause the machine 800 to perform any one or more of the techniques of the present disclosure, or that is capable of storing, encoding or carrying data structures used by or associated with such instructions. Non-limiting machine-readable medium examples may include solid-state memories, optical media, magnetic media, and signals (e.g., radio frequency signals, other photon-based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

Figure 9:
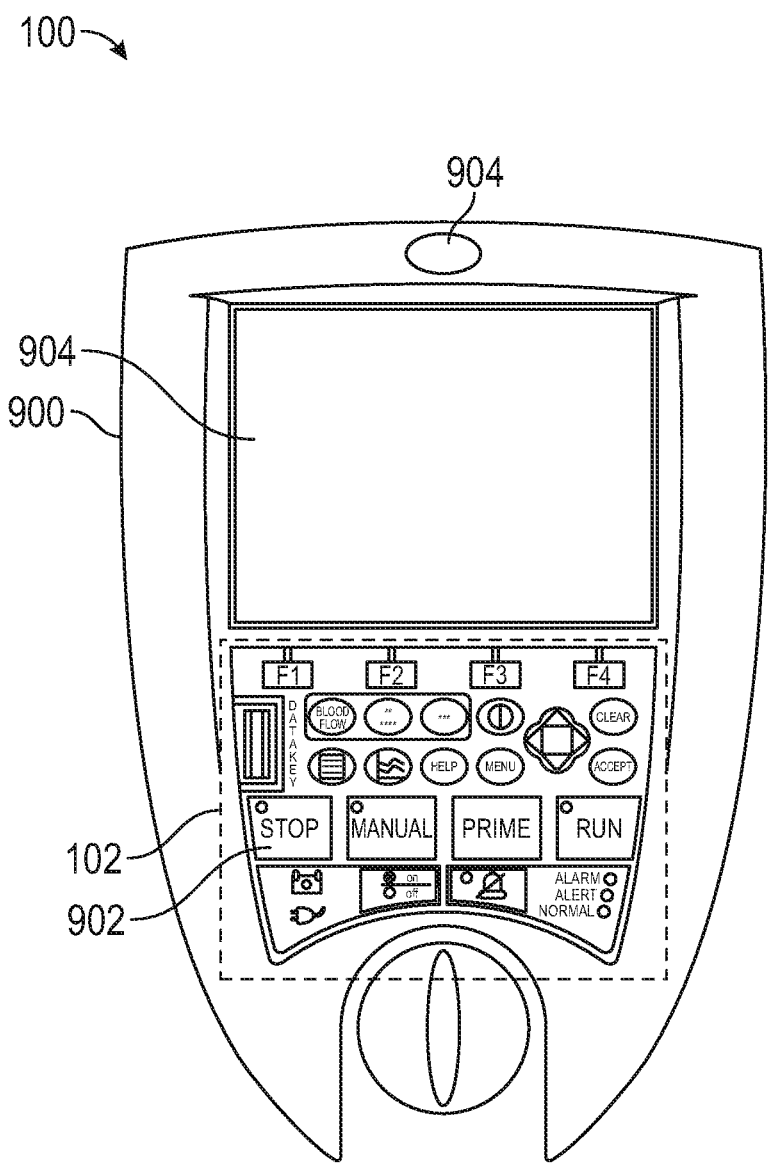
FIG. 9 shows a front view of an example of a system housing.

The instructions 824 may be further transmitted or received over a communications network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communications network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 800, and includes digital or analog communications signals or other intangible medium to facilitate communication of such software. A transmission medium is a machine-readable medium. FIG. 9 shows a front view of an example of a system housing 900. The blood filtration system 100 may include the system housing 900. The system housing 900 may include controls 902 (e.g., buttons, switches, or the like) that may change various operating parameters (or system parameters) of the blood filtration system 100. For instance, the controls 902 a button that operates the blood pump 112 (shown in FIG. 1). The system housing 900 may include the controller 102, and the controls 902 may communicate with the controller 102 to operate one or more components of the blood filtration system 100 (e.g., the blood pump 112 shown in FIG. 1, the harvesting pump 602 shown in FIG. 6, or the like). The controls 902 may communicate with the controller to adjust one or more system parameters for the blood filtration system 100, for instance a threshold (e.g., to adjust a speed of the blood pump 112, adjust a filtration rate, circuit fluid characteristic threshold, or the like).

As described herein, the controller 102 may generate a notification (e.g., by generating an electrical signal, or the like), for instance if the controller 102 determines that the infusion pump 130 has stopped pumping infusion fluid. For instance, the controller 102 may generate a notification based on a change in one or more of the pressure or flow rate of the infusion fluid. The controller 102 may generate a notification if the measured fluid characteristics exceeds the infusion fluid characteristic threshold. The controller 102 may generate a notification if the measured fluid characteristics exceeds the circuit fluid characteristic threshold.

In an example, the blood filtration system 100 may provide an auditory notification with a speaker 904. The blood filtration system 100 may provide a visual notification, for example with a display 906. The notification may prompt a user (e.g., a healthcare provider, patient or the like) to verify operation of the blood filtration system 100, for instance to facilitate maintenance of hemodynamic stability of a patient.

Figure 10:
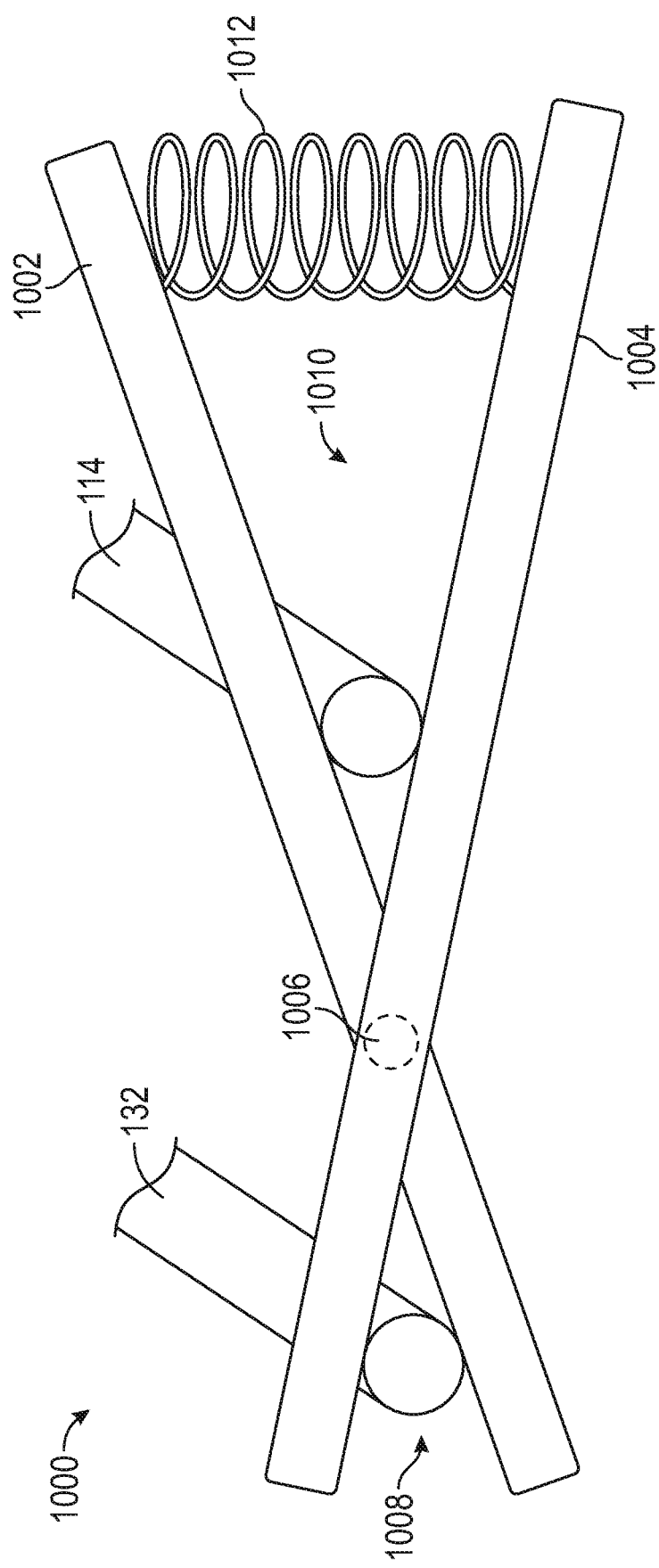
FIG. 10 shows a schematic view of an example of a clamp and the blood filtration system of FIG. 1.

FIG. 10 shows a schematic view of an example of a clamp 1000 and the blood filtration system 100. In an example, the clamp 1000 may couple with the blood circuit 103 (or the variable-volume blood circuit 200, shown in FIG. 2). The clamp 1000 may inhibit flow of infusion fluid into the blood circuit 103 (shown in FIG. 1). For example, the clamp 1000 may inhibit flow of infusion fluid into the blood circuit 103 when a speed of the filtration pump 116 exceeds a filtration rate threshold (e.g., when the filtration pump 116, shown in FIG. 1, stops). The clamp 1000 may inhibit flow of infusion fluid into the blood circuit 103 when pressure in the filtration line 114 exceeds a filtration line pressure threshold (e.g., when the pressure in the filtration line 114 equals, or is proximate to, ambient pressure).

The clamp 1000 may include a first blade 1002 and may include a second blade 1004. The blades 1002, 1004 may be rotatably coupled, for example with a hinge 1006. The blades 1002, 1004 may cooperate to inhibit flow of infusion fluid into the blood circuit 103. For instance, the infusion line 132 may be located on a first side 1008 of the hinge 1006. The filtration line 114 may be located on a second side 1010 of the hinge 1006. The blades 1002, 1004 may rotate, and the blades 1002, 1004 may compress the infusion line 132, for example to inhibit flow of infusion fluid in the infusion line 132. Accordingly, the clamp 1000 may inhibit flow of infusion fluid into the blood circuit 103.

The clamp 1000 may include a biasing member 1012 (e.g., an extension spring, compression spring, or the like). The biasing member 1012 may bias the blades 1002, 1004 toward compressing the infusion line 132. According, the clamp 1000 may be biased toward inhibiting flow in the infusion line 132.

The biasing member 1012 and the filtration line 114 may cooperate to allow flow of infusion fluid into the blood circuit 103. For example, when the filtration pump 116 is extracting filtrate fluid from the filter 110 (shown in FIG. 1), the filtration line 114 may be pressurized (and the pressure in the filtration line 114 does not exceed the filtration line pressure threshold). Accordingly, the filtration line 114 may exert a force on the blades 1002, 1004. The force applied by the filtration line 114 to the blades 1002, 1004 may overcome the bias provided by the biasing element. Accordingly, the force applied by the filtration line 114 when the filtration line 114 is pressurized may open the blades 1002, 1004 on the first side 1008 of the hinge 1006. In an example, the clamp 1000 allows the flow of infusion fluid in the infusion line 132 when the blades 1002, 1004 are open on the first side 1008 of the hinge 1006. Accordingly, the biasing member 1012 and the filtration line 114 may cooperate to allow flow of infusion fluid into the blood circuit 103

The biasing member 1012 may facilitate inhibiting the flow of infusion fluid into the blood circuit 103, for example when the pressure in the filtration line 114 exceeds a filtration line pressure threshold. For instance, the controller 102 may stop the filtration pump 116 (shown in FIG. 1). Because the filtration pump has stopped, pressure in the filtration line 114 may decrease. The decrease in pressure in the filtration line 114 may decrease the force applied to the blades 1002, 1004 on the second side 1010 of the hinge 1006. The decrease in force applied to the blades 1002, 1004 may cause the clamp 1000 to compress the infusion line 132 on the first side 1008 of the hinge 1006. In an example, the biasing member 1012 may be tuned to draw the blades 1002, 1004 together, for example when the pressure in the filtration line 114 exceeds the filtration line pressure threshold. Accordingly, the clamp 1000 may inhibit flow of infusion fluid in the infusion line 132 when the pressure in the filtration line 114 exceeds a filtration line pressure threshold (or when a speed of the filtration pump 116 exceeds a filtration rate threshold).

Figure 11:
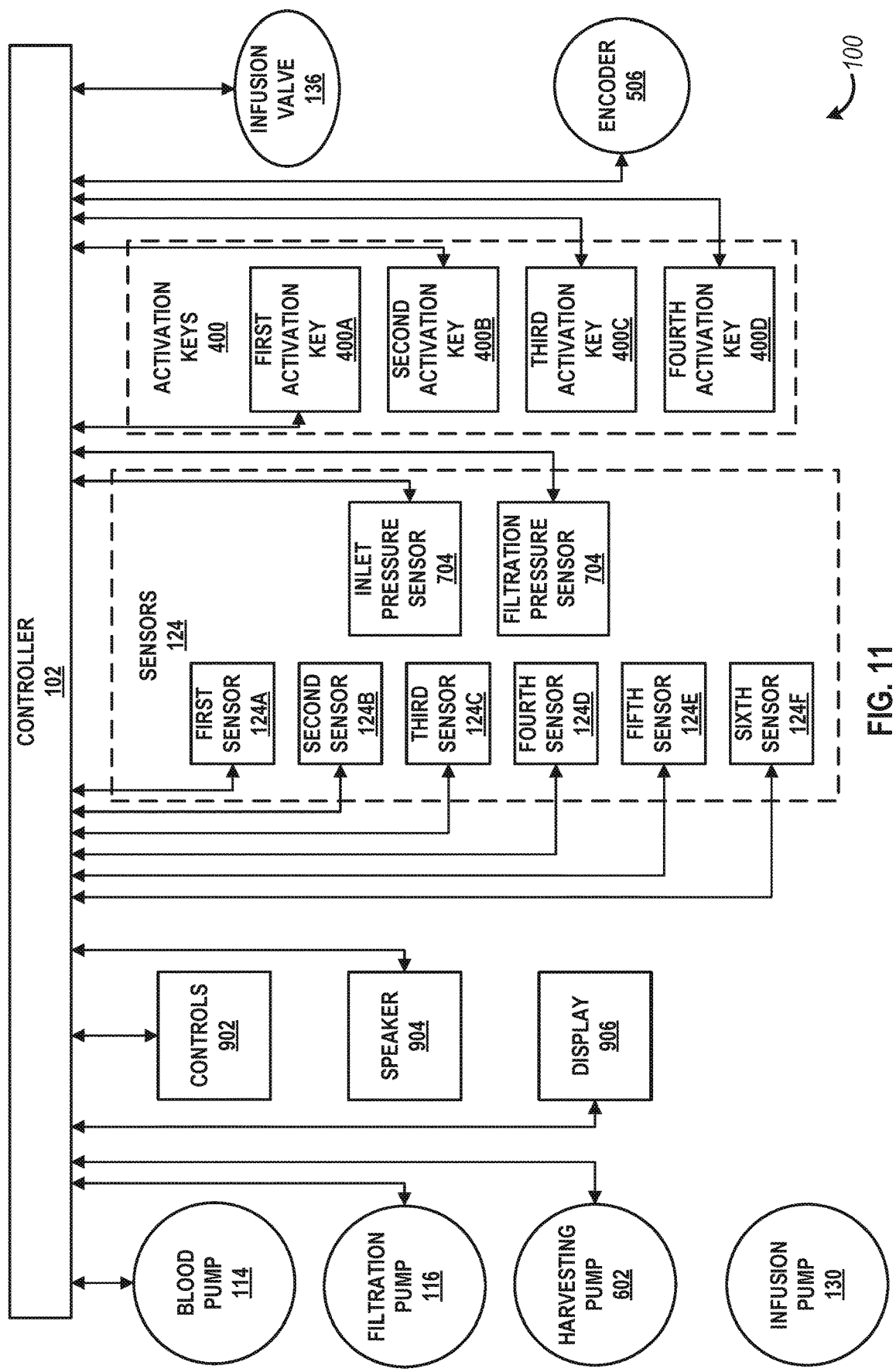
FIG. 11 shows a schematic view of yet another example of a blood filtration system.

FIG. 11 shows a schematic view of yet another example of a blood filtration system 100. The controller 102 may be in communication with the blood pump 112. The controller 102 may be in communication with the filtration pump 116. The controller 102 may be in communication with the harvesting pump 602. The controller 102 may be in communication with the harvesting pump 602. As described herein, the infusion pump 130 may be external to the blood filtration system 100. For instance, the controller 102 may not be in communication with the infusion pump controller 134.

The controller 102 may be in communication with the controls 902. The controller 102 may be in communication with the speaker 904. The controller 102 may be in communication with the display 906. The controller 102 may be in communication with the infusion valve 136. The controller 102 may be in communication with the encoder 506.

The controller 102 may be in communication with the one or more sensors 124. In an example, the controller 102 may be in communication with the first sensor 124A. The controller 102 may be in communication with the second sensor 124B. The controller 102 may be in communication with the third sensor 124C. The controller 102 may be in communication with the fourth sensor 124D. The controller 102 may be in communication with the fifth sensor 124E. The controller 102 may be in communication with the sixth sensor 124F. The controller 102 may be in communication with the inlet pressure sensor 704. The controller 102 may be in communication with the filtration pressure sensor 704.

The controller 102 may be in communication with the one or more activation keys 400. The controller 102 may be in communication with the first activation key 400A. The controller 102 may be in communication with the second activation key 400B. The controller 102 may be in communication with the third activation key 400C. The controller 102 may be in communication with the fourth activation key 400D.

The controller 102 may be in communication with other components of the blood filtration system 100. The controller 102 may be in communication with the interlink 830 (shown in FIG. 8). The controller 102 may facilitate communication between the components of the blood filtration system 100. The interlink 830 may facilitate communication between the components of the blood filtration system 100.

Figure 12:
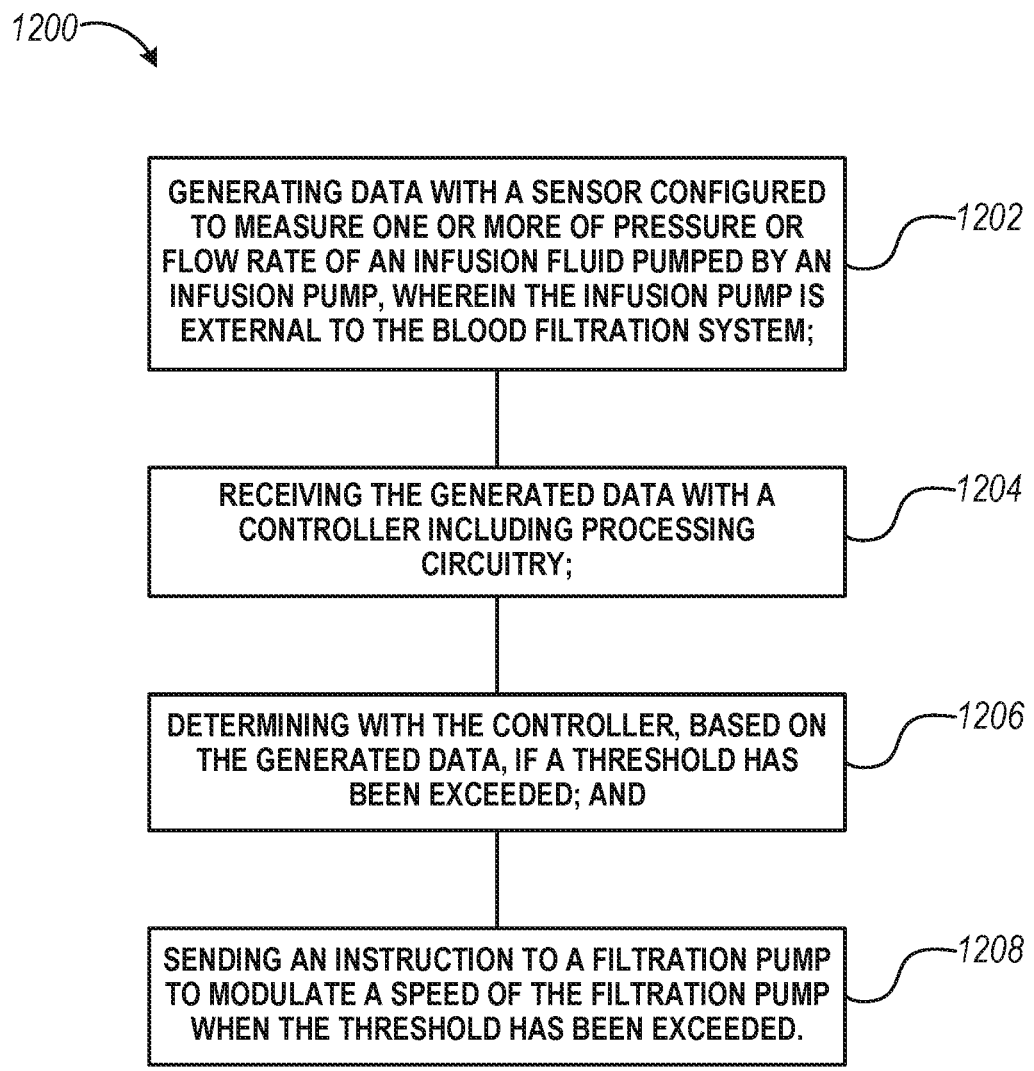
FIG. 12 shows one example of a method 1200 for controlling a blood filtration system.

FIG. 12 shows one example of a method 1200 for controlling a blood filtration system, including one or more of the blood filtration system 100 described herein. In describing the method 1200, reference is made to one or more components, features, functions and operations previously described herein. Where convenient, reference is made to the components, features, operations and the like with reference numerals. The reference numerals provided are exemplary and are not exclusive. For instance, components, features, functions, operations and the like described in the method 1200 include, but are not limited to, the corresponding numbered elements provided herein, and other corresponding elements described herein (both numbered and unnumbered) as well as their equivalents.

At 1202, data may be generated with a sensor (e.g., one or more of the sensors 124) that may be configured to measure one or more of pressure or flow rate of an infusion fluid pumped by an infusion pump 130. The infusion pump 130 may be external to the blood filtration system 100. The method 1200 may include at 1204 receiving the generated data with a controller 102 including processing circuitry. At 1206 the controller 102 may determine, based on the generated data, if a threshold has been exceeded. At 1208, an instruction may be sent, for example to a filtration pump 116 to modulate a speed of the filtration pump 116 when the threshold has been exceeded.

Figure 13:
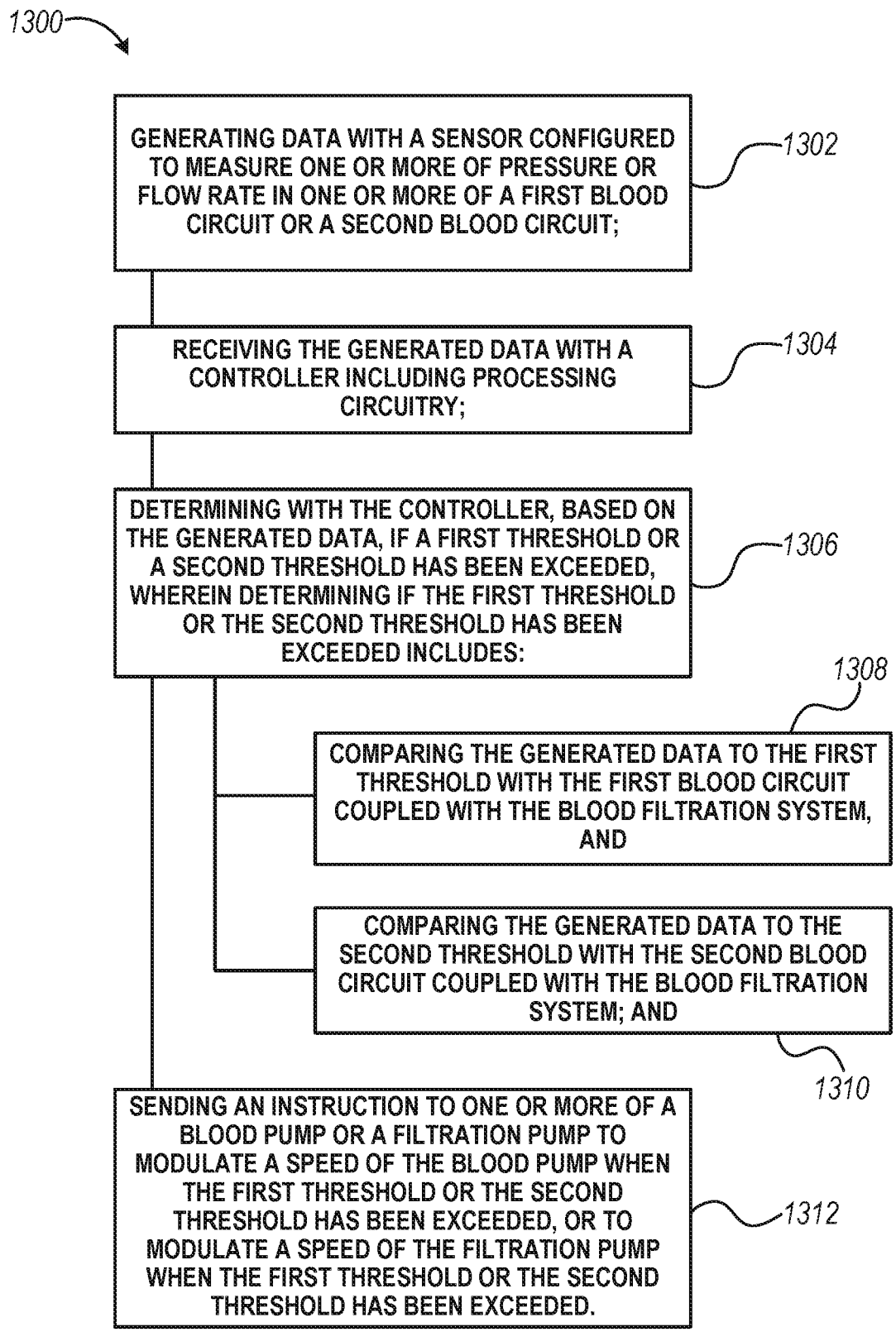
FIG. 13 shows one example of another method 1300 for controlling a blood filtration system.

FIG. 13 shows one example of another method 1300 for controlling a blood filtration system, including one or more of the blood filtration system 100 described herein. In describing the method 1300, reference is made to one or more components, features, functions and operations previously described herein. Where convenient, reference is made to the components, features, operations and the like with reference numerals. The reference numerals provided are exemplary and are not exclusive. For instance, components, features, functions, operations and the like described in the method 1300 include, but are not limited to, the corresponding numbered elements provided herein, and other corresponding elements described herein (both numbered and unnumbered) as well as their equivalents.

At 1302, data may be generated with a sensor (e.g., one or more of the sensors 124) that may be configured to measure one or more of pressure or flow rate in one or more of a first blood circuit (e.g., the variable-volume blood circuit 200 with the first withdrawal extension 200A coupled with the withdrawal line 104) or a second blood circuit (e.g., the variable-volume blood circuit 200 with the second withdrawal extension 200B coupled with the withdrawal line 104). The method 1300 may include at 1304 receiving the generated data with a controller 102 including processing circuitry. At 1306, the controller 102 may determine, based on the generated data, if a first threshold or a second threshold has been exceeded.

At 1308 determining if the first threshold or the second threshold has been exceeded may include comparing the generated data to the first threshold with the first blood circuit coupled with the blood filtration system 100. At 1310 determining if the first threshold or the second threshold has been exceeded may include comparing the generated data to the second threshold with the second blood circuit coupled with the blood filtration system 100. The method 1300 may include at 1312 that an instruction is sent to one or more of a blood pump 112 or a filtration pump 116, for example to modulate a speed of the blood pump 112 when the first threshold (or the second threshold) has been exceeded. An instruction may be sent to modulate a speed of the filtration pump 116 when the first threshold (or the second threshold) has been exceeded.

Figure 14:
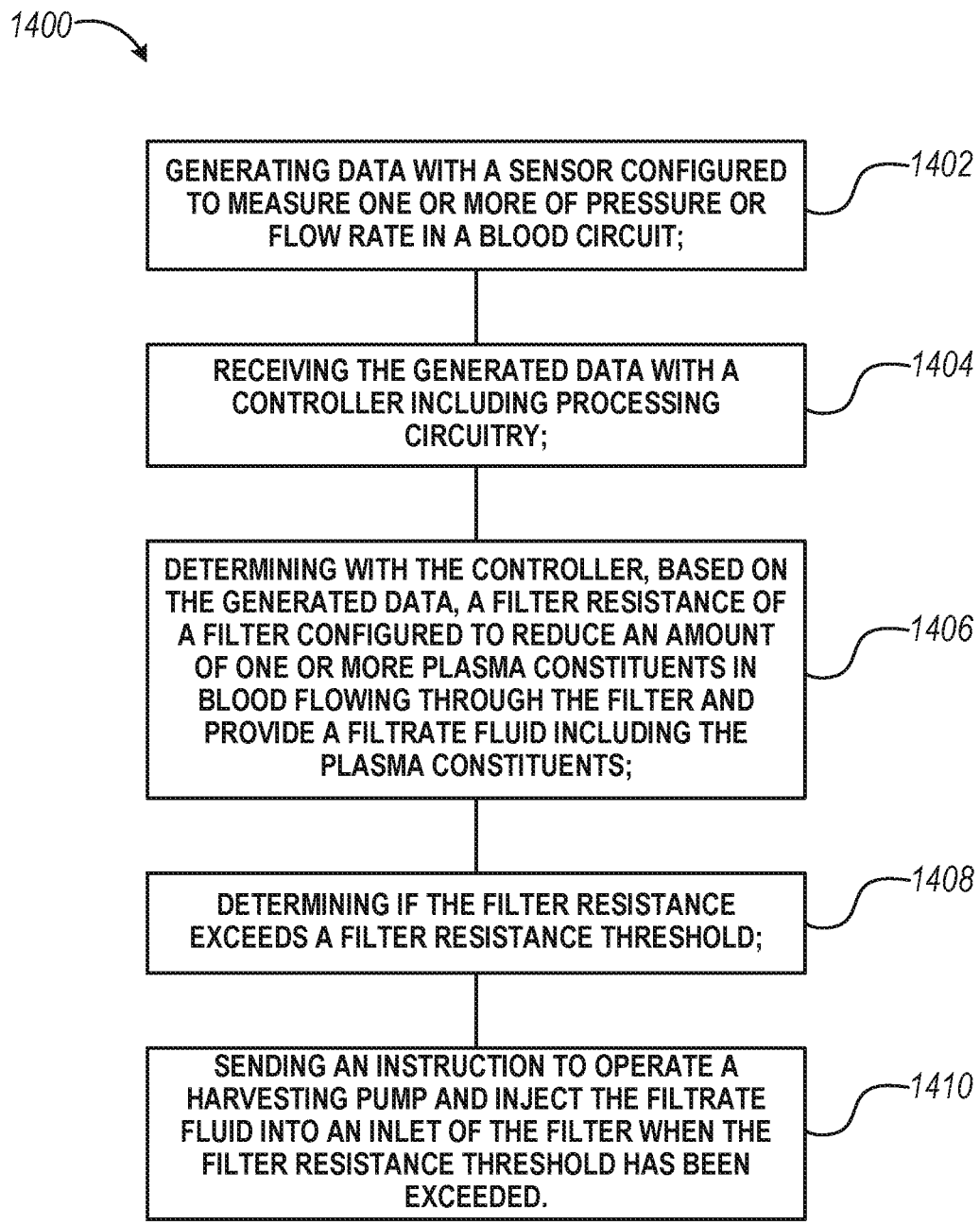
FIG. 14 shows one example of yet another method 1400 for controlling a blood filtration system.

FIG. 14 shows one example of yet another method 1400 for controlling a blood filtration system, including one or more of the blood filtration system 100 described herein. In describing the method 1400, reference is made to one or more components, features, functions and operations previously described herein. Where convenient, reference is made to the components, features, operations and the like with reference numerals. The reference numerals provided are exemplary and are not exclusive. For instance, components, features, functions, operations and the like described in the method 1400 include, but are not limited to, the corresponding numbered elements provided herein, and other corresponding elements described herein (both numbered and unnumbered) as well as their equivalents.

At 1402, the method 1400 may include generating data with a sensor (e.g., one or more of the sensors 124) configured to measure one or more of pressure or flow rate in a blood circuit (e.g., the blood circuit 103 or the variable-volume blood circuit 200). The method 1400 may include at 1404 that the generated data may be received with a controller 102 including processing circuitry. At 1406, the controller 102 may determine, based on the generated data, a filter resistance of a filter (e.g., the filter 110, the second filter 222, the filter 224, or the like) configured to reduce an amount of one or more plasma constituents in blood flowing through the filter and provide a filtrate fluid including the plasma constituents.

The method 1400 may include at 1408 determining if the filter resistance exceeds a filter resistance threshold. At 1410 an instruction may be sent (e.g., with the controller 102) to operate a harvesting pump 602. The harvesting pump 602 may inject the filtrate fluid into an inlet (e.g., filter inlet port 111A, or the like) of the filter when the filter resistance threshold has been exceeded.

Various Notes & Aspects

Aspect 1 is a blood filtration system configured to couple to an infusion pump that is external to the blood filtration system, the system configured to reduce one or more plasma constituents in blood of a patient, the blood filtration system comprising: a blood circuit configured to couple with the blood filtration system and including a catheter, a withdrawal line, and a return line, wherein the withdrawal line and the return line are configured to couple with the catheter, and the catheter is configured for insertion into a blood stream of the patient; an infusion port in communication with the blood circuit and configured to receive an infusion fluid pumped by the infusion pump; a variable-speed filtration pump configured to extract a filtrate fluid from a filter configured to reduce an amount of the one or more plasma constituents in blood flowing through the filter and provide the filtrate fluid including the filtered plasma constituents; a fluid characteristic sensor configured to be in fluidic communication with the infusion port and configured to measure one or more of pressure or flow rate of the infusion fluid pumped by the infusion pump; and a controller including processing circuitry configured to: monitor the fluid characteristic sensor to determine a change in one or more of the pressure or flow rate of the infusion fluid; and modulate a speed of the variable-speed filtration pump based on the change in one or more of the pressure or flow rate of the infusion fluid pumped by the infusion pump that is external to the blood filtration system.

In Aspect 2, the subject matter of Aspect 1 optionally includes wherein the infusion pump that is external to the blood filtration system is not modulated by the controller of the blood filtration system.

In Aspect 3, the subject matter of any one or more of Aspects 1-2 optionally include wherein the controller is not in communication with the infusion pump.

In Aspect 4, the subject matter of any one or more of Aspects 1-3 optionally include wherein the controller is configured to generate a notification if the change in one or more of the pressure or flow rate of the infusion fluid exceeds a fluid characteristic threshold.

In Aspect 5, the subject matter of any one or more of Aspects 1-4 optionally include wherein the controller is configured to stop the variable-speed filtration pump if the change in one or more of the pressure or flow rate of the infusion fluid exceeds a fluid characteristic threshold.

In Aspect 6, the subject matter of any one or more of Aspects 1-5 optionally include wherein the controller is configured to stop a variable-speed blood pump if the change in one or more of the pressure or flow rate of the infusion fluid exceeds a fluid characteristic threshold.

In Aspect 7, the subject matter of any one or more of Aspects 1-6 optionally include a gas detector configured to determine a presence of a discontinuity in flow of a liquid through the blood circuit and provide a gas detection signal to the controller, wherein the controller is configured to stop a variable-speed blood pump if the controller receives the gas detection signal.

In Aspect 8, the subject matter of any one or more of Aspects 1-7 optionally include wherein the blood circuit is a first blood circuit having a first total fluid capacity, and further comprising a second blood circuit having a second total fluid capacity.

In Aspect 9, the subject matter of Aspect 8 optionally includes wherein: the controller is configured to modulate the speed of the variable-speed filtration pump if the change in one or more of the pressure or flow rate of the infusion fluid exceeds a first fluid characteristic threshold with the first blood circuit coupled with the blood filtration system; and the controller is configured to modulate the speed of the variable-speed filtration pump if the change in one or more of the pressure or flow rate of the infusion fluid exceeds a second fluid characteristic threshold with the second blood circuit coupled with the blood filtration system.

In Aspect 10, the subject matter of any one or more of Aspects 8-9 optionally include wherein: the controller is configured to limit the speed of the variable-speed filtration pump at a first flow rate with the first blood circuit coupled with the blood filtration system; and the controller is configured to limit the speed of the variable-speed filtration pump at a second flow rate with the second blood circuit coupled with the blood filtration system.

In Aspect 11, the subject matter of any one or more of Aspects 8-10 optionally include wherein the first blood circuit includes a first filter having a first filter fluid capacity and the second blood circuit includes a second filter having a second filter fluid capacity.

In Aspect 12, the subject matter of Aspect 11 optionally includes wherein the controller is configured to: modulate a speed of the variable-speed filtration pump if the change in one or more of the pressure or flow rate of the infusion fluid exceeds a first fluid characteristic threshold with the first blood circuit coupled with the blood filtration system; and modulate the speed of the variable-speed filtration pump if the change in one or more of the pressure or flow rate of the infusion fluid exceeds a second fluid characteristic threshold with the second blood circuit coupled with the blood filtration system.

In Aspect 13, the subject matter of any one or more of Aspects 11-12 optionally include a variable-speed blood pump configured to pump blood in the withdrawal line, through the first filter or the second filter, and into the return line, wherein the controller is configured to: limit a speed of the variable-speed blood pump at a first speed with the first blood circuit coupled with the blood filtration system; and limit the speed of the variable-speed blood pump at a second speed with the second blood circuit coupled with the blood filtration system.

In Aspect 14, the subject matter of any one or more of Aspects 8-13 optionally include a circuit pressure sensor in communication with the controller and configured to measure a pressure in one or more of the first blood circuit or the second blood circuit, and wherein the controller is configured to: monitor the measured pressure in the first blood circuit with the first blood circuit coupled to the blood filtration system, or monitor the measured pressure in the second blood circuit with the second blood circuit coupled to the blood filtration system; and compare the measured pressure in the first blood circuit with a first circuit fluid characteristic threshold with the first blood circuit coupled with the blood filtration system, or compare the measure pressure in the second blood circuit to a second circuit fluid characteristic threshold with the second blood circuit coupled with the blood filtration system.

In Aspect 15, the subject matter of Aspect 14 optionally includes wherein the controller is configured to provide a notification if the measured pressure in the first blood circuit exceeds the first circuit fluid characteristic threshold, or provide a notification if the measured pressure in the second blood circuit exceeds the second circuit fluid characteristic threshold.

In Aspect 16, the subject matter of any one or more of Aspects 1-15 optionally include a valve configured to selectively inhibit flow of the infusion fluid into the infusion port of the blood circuit.

In Aspect 17, the subject matter of Aspect 16 optionally includes wherein the controller modulates the valve to inhibit flow of the infusion fluid into the infusion port if the change in one or more of the pressure or flow rate of the infusion fluid exceeds a fluid characteristic threshold.

In Aspect 18, the subject matter of any one or more of Aspects 16-17 optionally include wherein the controller modulates the valve to inhibit flow of the infusion fluid into the infusion port if the speed of the variable-speed filtration pump exceeds a speed threshold.

In Aspect 19, the subject matter of any one or more of Aspects 16-18 optionally include wherein the controller modulates the valve to inhibit flow of the infusion fluid into the infusion port if the variable-speed filtration pump is stopped.

Aspect 20 is a blood filtration system for reducing one or more plasma constituents in blood of a patient, the system comprising: a variable-volume blood circuit including: a catheter configured for insertion into a blood stream of the patient; a withdrawal line configured to couple with the catheter and having a first fluid capacity; a return line configured to couple with the catheter and having a second fluid capacity; a first filter configured to reduce an amount of one or more plasma constituents in blood flowing through the first filter and provide a filtrate fluid including the plasma constituents, wherein: the first filter has a third fluid capacity; the first withdrawal line and the first return line are configured to couple with the first filter; and one or more of a first withdrawal line extension, a first return line extension, or a second filter, wherein: the first withdrawal line extension has a fourth fluid capacity and is configured to couple with the withdrawal line to change a total fluid capacity of the variable-volume blood circuit; the first return line extension has a fifth fluid capacity and is configured to couple with the return line to change the total fluid capacity of the variable-volume blood circuit; and the second filter has a sixth fluid capacity and is interchangeable with the first filter to change the total fluid capacity of the variable-volume blood circuit.

In Aspect 21, the subject matter of Aspect 20 optionally includes wherein the total fluid capacity is a first total fluid capacity of the variable-volume blood circuit with the withdrawal line coupled with the first filter and the return line coupled to the first filter.

In Aspect 22, the subject matter of Aspect 21 optionally includes wherein the variable-volume blood circuit includes a second total fluid capacity with the first withdrawal line extension coupled to the withdrawal line, the withdrawal line coupled with the first filter, and the return line coupled with the first filter.

In Aspect 23, the subject matter of Aspect 22 optionally includes wherein the variable-volume blood circuit includes a third total fluid capacity with the withdrawal line coupled with the second filter and the return line coupled with the second filter.

In Aspect 24, the subject matter of Aspect 23 optionally includes wherein the variable-volume blood circuit includes a fourth total fluid capacity with the withdrawal line coupled with the first filter, the return line coupled with the first filter, and the first return line extension coupled with the return line.

In Aspect 25, the subject matter of any one or more of Aspects 21-24 optionally include wherein the variable-volume blood circuit includes a second total fluid capacity with the first withdrawal line coupled with the second filter and the first return line coupled with the second filter.

In Aspect 26, the subject matter of any one or more of Aspects 20-25 optionally include wherein fluid flow characteristics of a first withdrawal line extension are normalized with fluid flow characteristics of a second withdrawal line extension.

In Aspect 27, the subject matter of Aspect 26 optionally includes wherein a pressure differential across the first withdrawal line extension equals a pressure differential across the second withdrawal line extension.

In Aspect 28, the subject matter of Aspect 27 optionally includes wherein: the first withdrawal line has a first length and a first internal dimension to provide the first withdrawal line with a first pressure differential between a first end of the first withdrawal line and a second end of the first withdrawal line; and the second withdrawal line has a second length and a second internal dimension to provide the second withdrawal line with the first pressure differential between a first end of the second withdrawal line and a second end of the second withdrawal line.

In Aspect 29, the subject matter of any one or more of Aspects 19-28 optionally include an activation key coupled with the filter, wherein the controller is configured to communicate with the activation key to determine the total fluid capacity of the first filter.

Aspect 30 is a blood filtration system for reducing one or more plasma constituents in blood of a patient, the system comprising: a blood circuit including a catheter, a withdrawal line, and a return line, wherein the withdrawal line and the return line are configured to couple with the catheter, and the catheter is configured for insertion into a blood stream of the patient; a variable-speed peristaltic pump including one or more rollers configured to cyclically engage with at least a portion of the blood circuit to pump fluid in the withdrawal line, through a filter, and into the return line, wherein the filter is configured to reduce an amount of the one or more plasma constituents in blood flowing through the filter and provide a filtrate fluid including the filtered plasma constituents; and a controller including processing circuitry configured to modulate a speed of the peristaltic pump when the one or more rollers are proximate to the blood circuit to reduce pulsatile pressure changes in the blood circuit corresponding to the one or more rollers engaging with the blood circuit.

In Aspect 31, the subject matter of Aspect 30 optionally includes wherein the controller is configured to: decrease the speed of the peristaltic pump prior to roller disengagement from the blood circuit and reduce pulsatile pressure changes in the blood circuit corresponding to the roller disengaging from the blood circuit.

In Aspect 32, the subject matter of any one or more of Aspects 30-31 optionally include wherein the controller is configured to: decrease the speed of the peristaltic pump prior to the roller engaging with the blood circuit.

In Aspect 33, the subject matter of Aspect 32 optionally includes wherein the controller is configured to: increase the speed of the peristaltic pump when the roller is engaged with the blood circuit.

In Aspect 34, the subject matter of any one or more of Aspects 30-33 optionally include wherein the controller is configured to modulate the speed of peristaltic pump based on an angular position of the roller.

Aspect 35 is a blood filtration system for reducing one or more plasma constituents in blood of a patient, the system comprising: a filter configured to reduce an amount of one or more plasma constituents in blood flowing through the filter and provide a filtrate fluid including the plasma constituents, wherein the filter includes: a filter body; a blood inlet port included in the filter body and configured to couple with a withdrawal line, wherein the withdrawal line is configured to couple with a catheter and transmit blood from the patient; a blood outlet port included in the filter body and configured to couple with an infusion line, wherein the infusion line is configured to couple with the catheter and transmit blood to the patient; a filtrate fluid port included in the filter body and configured to couple with a harvest fluid line, wherein the filter is configured to transmit extracted filtrate fluid to the filtrate fluid port; and a harvesting port configured to receive filtrate fluid from the filtrate fluid port, the harvesting port in communication with the blood inlet port.

In Aspect 36, the subject matter of Aspect 35 optionally includes wherein the harvesting port is included in the filter body.

In Aspect 37, the subject matter of any one or more of Aspects 35-36 optionally include wherein the harvesting port is coupled with the blood inlet port.

In Aspect 38, the subject matter of Aspect 37 optionally includes a harvesting pump configured to pump filtrate fluid to the blood inlet port.

In Aspect 39, the subject matter of any one or more of Aspects 35-38 optionally include the catheter configured for insertion into a blood stream of the patient.

Aspect 40 is a blood filtration system for reducing one or more plasma constituents in blood of a patient, the system comprising: a controller including processing circuitry, wherein the controller is configured to: determine a filter resistance of a filter, wherein the filter is configured to reduce an amount of one or more plasma constituents in blood flowing through the filter and provide a filtrate fluid including the plasma constituents; determine if the filter resistance of the filter exceeds a first filter resistance threshold; operate a harvesting pump to extracted filtrate fluid from a filtrate reservoir and inject the filtrate fluid into an inlet of the filter to dilute the blood flowing through the filter; monitor the filter resistance of the filter; and operate the harvesting pump to stop injecting filtrate fluid into the inlet of the filter when the filter resistance exceeds a second filter resistance threshold.

In Aspect 41, the subject matter of Aspect 40 optionally includes wherein the controller is further configured to determine a blood flow rate of the blood flowing through the filter.

In Aspect 42, the subject matter of Aspect 41 optionally includes wherein the controller is further configured to: determine if the blood flow rate exceeds a first flow rate threshold; operate the harvesting pump to inject filtrate fluid into the inlet of the filter; monitor the blood flow rate; and operate the harvesting pump to stop injecting filtrate fluid into the inlet of the filter when the blood flow rate exceeds a second flow rate threshold.

In Aspect 43, the subject matter of any one or more of Aspects 40-42 optionally include wherein the controller is further configured to: monitor a rate of change of the filter resistance; and compare the rate of change of the filter resistance to a rate of change threshold.

In Aspect 44, the subject matter of any one or more of Aspects 40-43 optionally include wherein the controller is configured to: determine a withdrawal line resistance characteristic of the withdrawal line using a first pressure sensor in communication with the withdrawal line, the withdrawal line resistance characteristic corresponding to an amount of resistance to a flow of blood through the withdrawal line; determine an infusion line resistance characteristic of the infusion line using a second pressure sensor in communication with the infusion line, the infusion line resistance characteristic corresponding to an amount of resistance to a flow of blood through the infusion line; and provide a notification of one or more of the withdrawal line resistance characteristic or the infusion line resistance characteristic.

In Aspect 45, the subject matter of Aspect 44 optionally includes wherein the controller is configured to: determine a hematocrit value of the patient; determine a hemoconcentration resistance characteristic of the blood according to the determined hematocrit value of the patient, wherein the withdrawal line resistance characteristic or the infusion line resistance characteristic correspond in part to the hemoconcentration characteristic; and determine an occlusion resistance characteristic by subtracting the hemoconcentration resistance characteristic from the withdrawal line resistance characteristic or from the infusion line resistance characteristic.

In Aspect 46, the subject matter of Aspect 45 optionally includes wherein the notification of the one or more of the withdrawal line resistance characteristic or the infusion line resistance characteristic includes the occlusion resistance characteristic.

In Aspect 47, the subject matter of any one or more of Aspects 45-46 optionally include wherein the controller is configured to provide a notification of the occlusion resistance characteristic.

In Aspect 48, the subject matter of any one or more of Aspects 45-47 optionally include wherein determining the hematocrit value of the patient includes: controlling a speed of the blood pump and setting a flow rate of blood through the filter at a first blood flow rate; controlling the speed of the blood pump and setting the flow rate of blood through the filter at a second blood flow rate, wherein the first blood flow rate is different than the second blood flow rate; and determining the hematocrit at the second blood flow rate.

In Aspect 49, the subject matter of any one or more of Aspects 44-48 optionally include wherein the controller is configured to: compare the infusion line resistance or the withdrawal line resistance to a resistance threshold; and reduce a filtration rate or increase a blood flow rate if the withdrawal line resistance or the infusion line resistance exceeds the resistance threshold.

Aspect 50 is a method of controlling a blood filtration system, the method including: generating data with a sensor configured to measure one or more of pressure or flow rate of an infusion fluid pumped by an infusion pump, wherein the infusion pump is external to the blood filtration system; receiving the generated data with a controller including processing circuitry; determining with the controller, based on the generated data, if a threshold has been exceeded; and sending an instruction to a filtration pump to modulate a speed of the filtration pump when the threshold has been exceeded.

Aspect 51 is a method of controlling a blood filtration system, the method including: generating data with a sensor configured to measure one or more of pressure or flow rate in one or more of a first blood circuit or a second blood circuit; receiving the generated data with a controller including processing circuitry; determining with the controller, based on the generated data, if a first threshold or a second threshold has been exceeded, wherein determining if the first threshold or the second threshold has been exceeded includes: comparing the generated data to the first threshold with the first blood circuit coupled with the blood filtration system, and comparing the generated data to the second threshold with the second blood circuit coupled with the blood filtration system; and sending an instruction to one or more of a blood pump or a filtration pump to modulate a speed of the blood pump when the first threshold or the second threshold has been exceeded, or to modulate a speed of the filtration pump when the first threshold or the second threshold has been exceeded.

Aspect 52 is a method of controlling a blood filtration system, the method including: generating data with a sensor configured to measure one or more of pressure or flow rate in a blood circuit; receiving the generated data with a controller including processing circuitry; determining with the controller, based on the generated data, a filter resistance of a filter configured to reduce an amount of one or more plasma constituents in blood flowing through the filter and provide a filtrate fluid including the plasma constituents; determining if the filter resistance exceeds a filter resistance threshold; and sending an instruction to operate a harvesting pump and inject the filtrate fluid into an inlet of the filter when the filter resistance threshold has been exceeded.

Each of these non-limiting aspects may stand on its own, or may be combined in various permutations or combinations with one or more of the other aspects.

The above description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

The claimed invention is:

1. A blood filtration system configured to couple to an infusion pump that is external to the blood filtration system, the system configured to reduce one or more plasma constituents in blood of a patient, the blood filtration system comprising:
   a blood circuit configured to couple with the blood filtration system and including a catheter, a withdrawal line, and a return line, wherein the withdrawal line and the return line are configured to couple with the catheter, and the catheter is configured for insertion into a blood stream of the patient;
   an infusion port in communication with the blood circuit and configured to receive an infusion fluid pumped by the infusion pump;
   a variable-speed filtration pump configured to extract a filtrate fluid from a filter configured to reduce an amount of the one or more plasma constituents in blood flowing through the filter and provide the filtrate fluid including the filtered plasma constituents;
   a fluid characteristic sensor configured to be in fluidic communication with the infusion port and configured to measure one or more of pressure or flow rate of the infusion fluid at the infusion port; and
   a controller including processing circuitry configured to:
      monitor the fluid characteristic sensor to determine a change in one or more of the pressure or flow rate of the infusion fluid at the infusion port;
      modulate a speed of the variable-speed filtration pump based on the change in one or more of the pressure or flow rate of the infusion fluid at the infusion port-; and
      wherein the controller is not in communication with the infusion pump.

2. The blood filtration system of claim 1, wherein the infusion pump that is external to the blood filtration system is not modulated by the controller of the blood filtration system.

3. The blood filtration system of claim 1, wherein the controller is configured to generate a notification if the change in one or more of the pressure or flow rate of the infusion fluid exceeds a fluid characteristic threshold.

4. The blood filtration system of claim 1, wherein the controller is configured to stop the variable-speed filtration pump if the change in one or more of the pressure or flow rate of the infusion fluid exceeds a fluid characteristic threshold.

5. The blood filtration system of claim 1, wherein the controller is configured to stop a variable-speed blood pump if the change in one or more of the pressure or flow rate of the infusion fluid exceeds a fluid characteristic threshold.

6. The blood filtration system of claim 1, further comprising a gas detector configured to determine a presence of a discontinuity in flow of a liquid through the blood circuit and provide a gas detection signal to the controller, wherein the controller is configured to stop a variable-speed blood pump if the controller receives the gas detection signal.

7. The blood filtration system of claim 1, wherein the blood circuit is a first blood circuit having a first total fluid capacity, and further comprising a second blood circuit having a second total fluid capacity.

8. The blood filtration system of claim 7, wherein:
the controller is configured to modulate the speed of the variable-speed filtration pump if the change in one or more of the pressure or flow rate of the infusion fluid exceeds a first fluid characteristic threshold with the first blood circuit coupled with the blood filtration system; and
the controller is configured to modulate the speed of the variable-speed filtration pump if the change in one or more of the pressure or flow rate of the infusion fluid exceeds a second fluid characteristic threshold with the second blood circuit coupled with the blood filtration system.

9. The blood filtration system of claim 7, wherein:
the controller is configured to limit the speed of the variable-speed filtration pump at a first flow rate with the first blood circuit coupled with the blood filtration system; and
the controller is configured to limit the speed of the variable-speed filtration pump at a second flow rate with the second blood circuit coupled with the blood filtration system.

10. The blood filtration system of claim 7, wherein the first blood circuit includes a first filter having a first filter fluid capacity and the second blood circuit includes a second filter having a second filter fluid capacity.

11. The blood filtration system of claim 10, wherein the controller is configured to:
modulate a speed of the variable-speed filtration pump if the change in one or more of the pressure or flow rate of the infusion fluid exceeds a first fluid characteristic threshold with the first blood circuit coupled with the blood filtration system; and
modulate the speed of the variable-speed filtration pump if the change in one or more of the pressure or flow rate of the infusion fluid exceeds a second fluid characteristic threshold with the second blood circuit coupled with the blood filtration system.

12. The blood filtration system of claim 2, further comprising a variable-speed blood pump configured to pump blood in the withdrawal line, through the first filter or the second filter, and into the return line, wherein the controller is configured to:
limit a speed of the variable-speed blood pump at a first speed with the first blood circuit coupled with the blood filtration system; and
limit the speed of the variable-speed blood pump at a second speed with the second blood circuit coupled with the blood filtration system.

13. The blood filtration system of claim 7, further comprising a circuit pressure sensor in communication with the controller and configured to measure a pressure in one or more of the first blood circuit or the second blood circuit, and wherein the controller is configured to:
monitor the measured pressure in the first blood circuit with the first blood circuit coupled to the blood filtration system, or monitor the measured pressure in the second blood circuit with the second blood circuit coupled to the blood filtration system; and
compare the measured pressure in the first blood circuit with a first circuit fluid characteristic threshold with the first blood circuit coupled with the blood filtration system, or compare the measured pressure in the second blood circuit to a second circuit fluid characteristic threshold with the second blood circuit coupled with the blood filtration system.

14. The blood filtration system of claim 13, wherein the controller is configured to provide a notification if the measured pressure in the first blood circuit exceeds the first circuit fluid characteristic threshold, or provide a notification if the measured pressure in the second blood circuit exceeds the second circuit fluid characteristic threshold.

15. The blood filtration system of claim 1, further comprising a valve configured to selectively inhibit flow of the infusion fluid into the infusion port of the blood circuit.

16. The blood filtration system of claim 15, wherein the controller modulates the valve to inhibit flow of the infusion fluid into the infusion port if the change in one or more of the pressure or flow rate of the infusion fluid exceeds a fluid characteristic threshold.

17. The blood filtration system of claim 15, wherein the controller modulates the valve to inhibit flow of the infusion fluid into the infusion port if the speed of the variable-speed filtration pump exceeds a speed threshold.

18. The blood filtration system of claim 15, wherein the controller modulates the valve to inhibit flow of the infusion fluid into the infusion port if the variable-speed filtration pump is stopped.

* * * * *